(12) United States Patent
Paré et al.

(10) Patent No.: US 10,162,107 B2
(45) Date of Patent: Dec. 25, 2018

(54) MULTICORE OPTICAL FIBER FOR MULTIPOINT DISTRIBUTED SENSING AND PROBING

(71) Applicant: INSTITUT NATIONAL D'OPTIQUE, Québec (CA)

(72) Inventors: Claude Paré, Québec (CA); Patrick Paradis, Québec (CA); Chiara Meneghini, Québec (CA); Antoine Proulx, Québec (CA)

(73) Assignee: INSTITUT NATIONAL D'OPTIQUE, Quebec, Quebec (CA)

( * ) Notice: Subject to any disclaimer, the term of this patent is extended or adjusted under 35 U.S.C. 154(b) by 158 days.

(21) Appl. No.: 15/434,530

(22) Filed: Feb. 16, 2017

(65) Prior Publication Data
US 2018/0231712 A1 Aug. 16, 2018

(51) Int. Cl.
*G02B 6/02* (2006.01)
*G02B 6/26* (2006.01)
*G01J 1/04* (2006.01)

(52) U.S. Cl.
CPC ........ *G02B 6/02042* (2013.01); *G01J 1/0425* (2013.01); *G02B 6/02076* (2013.01); *G02B 6/26* (2013.01)

(58) Field of Classification Search
CPC .. G02B 6/02042; G02B 6/26; G02B 6/02076; G01J 1/0425
See application file for complete search history.

(56) References Cited

U.S. PATENT DOCUMENTS

| | | | |
|---|---|---|---|
| 4,443,698 A | 4/1984 | Shiffner | |
| 4,618,211 A | 10/1986 | Fleury | |
| 4,997,247 A | 3/1991 | Stowe | |
| 5,625,728 A | 4/1997 | Tardy et al. | |
| 6,865,320 B1 | 3/2005 | Westbrook | |
| 7,085,451 B2 | 8/2006 | Gaylord et al. | |
| 7,209,605 B2 * | 4/2007 | Cantin | G01D 5/35383 374/E11.016 |
| 7,792,392 B2 | 9/2010 | Chen et al. | |

(Continued)

OTHER PUBLICATIONS

Pisanello, F. et al., "Multipoint-Emitting Optical Fibers for Spatially Adressable In Vivo Optogenetics", NeuroResource, Neuron, Jun. 18, 2014, vol. 82 p. 1245-1254, Elsevier Inc.

(Continued)

*Primary Examiner* — Tony Ko
(74) *Attorney, Agent, or Firm* — Merchant & Gould P.C.

(57) ABSTRACT

A multicore optical fiber includes a cladding and multiple cores disposed in the cladding. Each core has a light-guiding path and follows a helical trajectory about a fiber axis. The multicore fiber also includes a set of discrete lateral coupling zones, which are longitudinally distributed and azimuthally aligned with respect to the fiber axis. Each lateral coupling zone forms an optical coupling path, which enables at least one of lateral in-coupling and out-coupling of light between a corresponding one of the cores and an exterior of the multicore fiber. An optical probing system for light delivery to and/or light collection from a probed region includes a multicore optical fiber to enable coupling of guided light out of the cores for delivery to the probed region and/or collection of light from the probed region for coupling into one of the cores.

27 Claims, 20 Drawing Sheets

(56) References Cited

U.S. PATENT DOCUMENTS

| | | |
|---|---|---|
| 7,883,535 B2 | 2/2011 | Cantin et al. |
| 7,889,960 B2 | 2/2011 | De Montmorillon et al. |
| 8,582,943 B2 | 11/2013 | Alkemper et al. |
| 8,630,515 B2 | 1/2014 | Childers et al. |
| 8,725,001 B2 | 5/2014 | Fini et al. |
| 8,792,978 B2 | 7/2014 | Wells et al. |
| 9,109,969 B2 | 8/2015 | Kreger et al. |
| 9,146,346 B2 | 9/2015 | Paré et al. |
| 9,188,745 B2 | 11/2015 | Pimpinella et al. |
| 9,435,942 B2 | 9/2016 | Westbrook |
| 2004/0056183 A1 | 3/2004 | Eggleton et al. |
| 2006/0147153 A1 | 7/2006 | Sahlgren et al. |
| 2007/0047875 A1 | 3/2007 | Sezerman et al. |
| 2007/0110367 A1 | 5/2007 | Walker et al. |
| 2007/0201793 A1 | 8/2007 | Askins et al. |
| 2008/0079940 A1* | 4/2008 | Sezerman ........... C03C 23/0025 356/364 |
| 2011/0129190 A1 | 6/2011 | Fini et al. |
| 2012/0099112 A1 | 4/2012 | Alphonse et al. |
| 2014/0178018 A1 | 6/2014 | Matsuo |
| 2015/0147025 A1 | 5/2015 | Westbrook |
| 2016/0231508 A1* | 8/2016 | Butler ..................... G02B 6/34 |

OTHER PUBLICATIONS

Pruneri, V. et al., "Fiber and Integrated Waveguide-Based Optical Sensors", Journal of Sensors, 2009, 185 pages, Hindawi Publishing Corporation.

Weng, Y. et al., "Advanced Spatial-Division Multiplexed Measurement Systems Propositions—From Telecommunication to Sensing Applications: A Review", Sensors, 2016, vol. 16, No. 1387, p. 1-35.

Westbrook, P.S. et al., "Integrated optical fiber shape sensor modules based on twisted multicore fiber grating arrays", Optical Fibers and Sensors for Medica Diagnostics and Treatment Applications XIV, Proc. of SPIE, 2014, vol. 8938, 7 pages.

Zhang, H. et al., "A multi-core fiber to single-mode fiber side-polished coupler", Conference Paper, ResearchGate, Jun. 2016, 3 pages, https://www.researchgate.net/publication/299397789.

Zhou, K. et al., "Low thermal sensitivity grating devices based on ex-45° tilting structure capable of forward propagating cladding modes coupling", Journal of Lightware Technology, Jan. 15, 2007, vol. 24, Issue 12, p. 5087-5094.

* cited by examiner

MULTICORE OPTICAL FIBER FOR MULTIPOINT DISTRIBUTED SENSING AND PROBING

TECHNICAL FIELD

The technical field generally relates to optical fibers, and more particularly to optical fibers for use in multipoint quasi-distributed sensing and probing applications.

BACKGROUND

Quasi-distributed fiber-optic sensors and probes enabling multipoint light delivery to and/or light collection from a region of interest have found applications in various fields. Examples of fields include medicine, optogenetics, biological and chemical sensing, environmental and structural monitoring, oil and gas industry, military, and transportation. These sensors and probes can provide various advantages including immunity to electromagnetic interference, electrical passivity, small size and light weight, resistance to harsh environments, and possibility of multiplexed operation. However, existing quasi-distributed fiber-optic sensors and probes also possess limitations in terms of sensitivity and spatial resolution, especially for applications in space-confined and other restricted environments in which compact multipoint sensing and probing is required or desired. Challenges therefore remain in the development of optical fibers for use in quasi-distributed sensing and probing applications.

SUMMARY

The present description generally relates to techniques using a multicore optical fiber for light delivery and collection via a linear array of lateral coupling zones longitudinally distributed parallel to the fiber axis and azimuthally aligned with one another. Each one of the lateral coupling zones enables light to be laterally coupled to and/or from a corresponding core of the multicore optical fiber.

In accordance with an aspect, there is provided a multicore optical fiber having a fiber axis, the multicore optical fiber including:
 a cladding;
 multiple cores disposed in the cladding, each one of the multiple cores following a helical trajectory about the fiber axis; and
 a set of lateral coupling zones longitudinally distributed and azimuthally aligned with respect to the fiber axis, each one of the lateral coupling zones forming an optical coupling path extending and enabling lateral coupling of light between a corresponding one of the multiple cores and an exterior of the multicore optical fiber.

In some implementations, at least one of the lateral coupling zones includes a cavity extending inwardly from an outer lateral surface of the multicore optical fiber toward a corresponding one of the multiple cores.

In some implementations, the cavity extends at least partly into the corresponding core and defines an optical interface therebetween.

In some implementations, the optical interface is oriented with respect to the corresponding core to enable the lateral coupling of light to be effected via total internal reflection inside the corresponding core at the optical interface.

In some implementations, the at least one of the lateral coupling zones further includes a light reflector disposed inside the cavity and along the optical coupling path.

In some implementations, the light reflector includes a reflective layer deposited on a wall of the cavity.

In some implementations, the light reflector includes a reflective microsphere.

In some implementations, the cavity is filled at least partly with a material having a refractive index different than a refractive index of the corresponding core.

In some implementations, the at least one of the lateral coupling zones further includes focusing optics arranged on the outer lateral surface of the multicore optical fiber and extending over and across an opening of the cavity.

In some implementations, the cavity is spaced outwardly from the corresponding core in a manner such that a lateral gap is formed therebetween, the lateral gap enabling evanescent wave coupling of light thereacross between the corresponding core and the exterior of the multicore fiber.

In some implementations, the cavity is formed by laser processing.

In some implementations, at least one of the lateral coupling zones includes a light deflector arranged in the corresponding core.

In some implementations, the light deflector includes a fiber Bragg grating, the fiber Bragg grating having a grating axis tilted with respect to a light-guiding path of the corresponding core.

In some implementations, in a cross-section transverse to the fiber axis, the multiple cores are arranged along a perimeter of a closed-shape figure centered with respect to the fiber axis.

In some implementations, at least one of the lateral coupling zones is configured to couple light from the corresponding one of the multiple cores to the exterior of the multicore optical fiber.

In some implementations, at least one of the lateral coupling zones is configured to couple light from the exterior of the multicore optical fiber to the corresponding one of the multiple cores.

In some implementations, at least one of the lateral coupling zones is configured to couple light both out of and into the corresponding one of the multiple cores.

In some implementations, the helical trajectory of each core has a spatial repetition period ranging from 5 millimeters (mm) to 50 centimeters (cm).

In some implementations, adjacent ones of the lateral coupling zones are spaced-apart by a distance ranging from 100 micrometers (pm) to 10 cm.

In some implementations, the lateral coupling zones are uniformly spaced-apart.

In some implementations, the multiple cores include between 2 and 50 cores.

In some implementations, the helical trajectories followed by the multiple cores result from a permanent spin imparted to the multicore optical fiber.

In some implementations, each one of the multiple cores follows the helical trajectory along an entire length thereof.

In some implementations, each one of the multiple cores follows the helical trajectory along a partial length thereof.

In some implementations, the multicore optical fiber further includes a centered core coaxially aligned with and following a straight trajectory along the fiber axis.

In accordance with another aspect, there is provided an optical probing system for at least one of light delivery to and light collection from a probed region. The optical probing system includes a multicore optical fiber having a fiber axis and including a cladding, multiple cores disposed in the cladding and extending helically about the fiber axis, and a set of lateral coupling zones longitudinally distributed and azimuthally aligned with respect to the fiber axis. Each one of the lateral coupling zones forms an optical coupling path enabling at least one of:

lateral coupling of guided light out of a corresponding one of the multiple cores for delivery to the probed region; and collection of incoming light from the probed region for lateral coupling into the corresponding one of the multiple cores.

In some implementations, the optical probing system further includes a light injection assembly configured to inject the guided light into the multiple cores.

In some implementations, the optical probing system further includes a light detection assembly configured to receive the collected light from the multiple cores.

In some implementations, the optical probing system further includes an additional set of lateral coupling zones and at least one of:

a light injection assembly coupled to the additional set of lateral coupling zones and configured to inject the guided light into the multiple cores; an a light detection assembly coupled to the additional set of lateral coupling zones and configured to receive the collected incoming light from the multiple cores.

Other features and advantages of the present description will become more apparent upon reading of the following non-restrictive description of specific embodiments thereof, given by way of example only with reference to the accompanying drawings.

DETAILED DESCRIPTION

Figure 1:
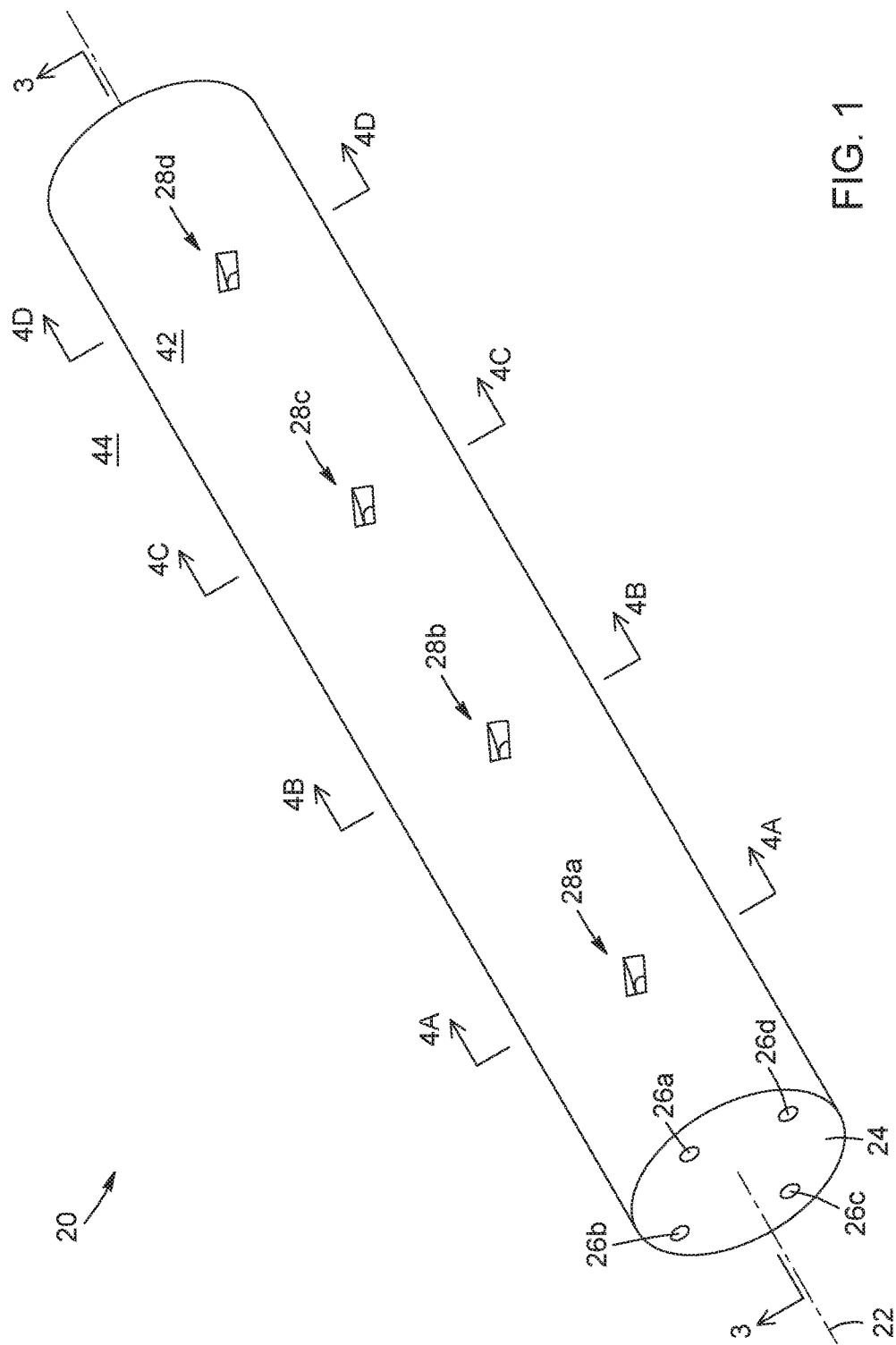
FIG. 1 is a schematic perspective view of a multicore optical fiber, in accordance with an exemplary embodiment.
Figure 2:
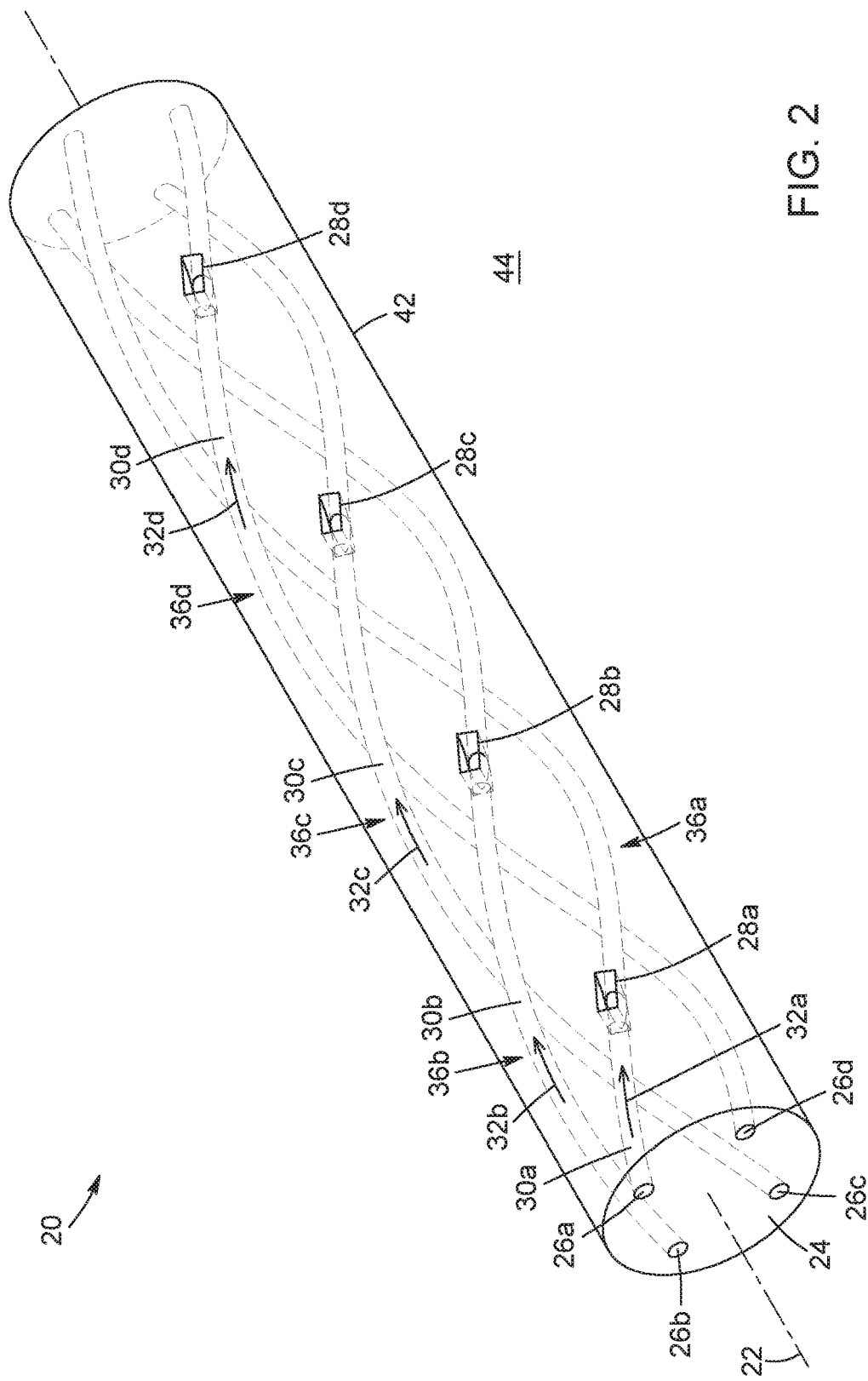
FIG. 2 is another schematic perspective view of the multicore optical fiber of FIG. 1, wherein the cladding is shown as being transparent to better illustrate the helical trajectories followed by the multiple cores around the fiber axis.

In the following description, similar features in the drawings have been given similar reference numerals and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The present description generally relates to a multicore optical fiber. The multicore optical fiber includes multiple cores disposed in a cladding and having at least a portion thereof following a helical trajectory along the length of the fiber. The multicore optical fiber also includes a set of longitudinally distributed and azimuthally aligned lateral coupling zones for enabling lateral optical coupling between the multiple cores and the outside of the fiber. The present description also generally relates to an optical fiber-based probing system including such a multicore optical fiber for at least one of light delivery to and light collection from a probed region.

The present techniques can be used in a variety of multipoint quasi-distributed fiber-based sensing and probing applications where it is desirable to provide lateral optical coupling. The present techniques can be implemented in various types of fiber-based systems intended for use in fields such as, for example and without limitation, biophotonics, chemical sensing, telecommunications (e.g., for coupling with an array of injection laser diodes), and spectroscopy. Non-limiting examples of possible applications include: delivery of optically encoded stimulation signals for medical applications (e.g., optical cochlear neuron stimulation) with millimetric or sub-millimetric spatial resolution; depth-dependent analysis of tissue; or depth-dependent spatial addressing at high spatial or high spectral resolution in optogenetics or fiber endoscopy, with or without recollection of the optical signal emitted from the sample under test; light delivery to and/or light collection from a series of densely packed photonic integrated circuits; and light injection into a multicore fiber from a linear array of fibers or directly from a linear laser diode array or a set of planar micro-chips for sensing or telecommunication applications.

In the present description, the terms "quasi-distributed" is intended to refer to the fact that the multicore optical fiber disclosed herein enables lateral coupling of light between the multiple cores and the environment at discrete, spaced-apart locations that are longitudinally distributed along the fiber axis.

In the present description, the term "optical probe" and variants thereof are intended to refer to any optical system or device which can deliver optical energy to a region of interest and/or collect optical energy from the region of interest. More particularly, the term "optical probe" and variants thereof is meant to encompass optical systems and devices used solely for light delivery, optical systems and devices used solely for light collection, and optical systems and devices used for both light delivery and light collection.

In the present description, the terms "light" and "optical" are intended to refer to radiation in any appropriate region of the electromagnetic spectrum. The terms "light" and "optical" are therefore not limited to visible light, but can include, for example, the infrared wavelength range. For example, in some embodiments, the signals guided by the multicore optical fiber can have wavelengths ranging from about 400 nm to about 1800 nm. Of course, other wavelength ranges may be considered in other embodiments.

In the present description, the terms "longitudinal" and "axial", and variants thereof, are intended to refer to a direction that is parallel or near parallel to the length of the multicore optical fiber. Meanwhile, the terms "transverse", "lateral" and "radial", and variants thereof, are intended to refer to a direction that lies in a plane perpendicular or substantially perpendicular to the length of the multicore optical fiber and to the longitudinal and axial directions as just defined.

Multicore Optical Fiber

Referring to FIGS. 1 to 3 and 4A to 4D, there is illustrated an exemplary embodiment of a multicore optical fiber 20 having a fiber axis 22. For brevity, the expression "multicore optical fiber" may, in some instances, be shortened to "multicore fiber", "optical fiber" or simply "fiber". It is also noted that the term "fiber axis" may be used interchangeably with the terms "longitudinal axis" and "longitudinal fiber axis".

The multicore fiber 20 generally includes a cladding 24, multiple off-centered cores 26a to 26d embedded in the cladding 24, and a set of lateral coupling zones 28a to 28d distributed at spaced-apart intervals parallel to the fiber axis 22. Each lateral coupling zone 28a to 28d enables in-coupling of light to and/or out-coupling of light from a corresponding one of the cores 26a to 26d. More detail regarding the structure, configuration and operation of these and other possible components of the multicore optical fiber 20 will be provided below.

For ease of representation, the multicore optical fiber 20 illustrated in FIGS. 1 to 3 and 4A to 4D includes only four cores 26a to 26d disposed in a single-layer cladding 24 having a circular outer contour. However, depending on the application, the cladding 24 may have a circular or non-circular geometry, and may have either a single-layer structure or a multilayer structure (e.g., double-clad and triple-clad structures). Also, in other embodiments, the fiber 20 can include two, three or more than four cores. In some non-limiting embodiments, the multicore fiber 20 can include between 2 and 50 cores, for example between 6 and 18 cores.

In the embodiment of FIGS. 1 to 3 and 4A to 4D, the cores 26a to 26d form light-guiding paths 30a to 30d along which respective optical signals 32a to 32d are guided. To this end, each of the cores 26a to 26d is made of a material having a refractive index higher than the refractive index of the cladding material. Depending on the application, the multicore fiber 20 can have various cladding and core compositions and exhibit different refractive index profiles (e.g., graded-index profile or a step-index profile). For example, in some embodiments, the cladding 24 can be made of pure silica and the cores 26a to 26d can be made of silica containing one or more index-changing dopants (e.g., rare-earth dopant materials such as erbium, ytterbium and thulium in the case of active fibers, and $GeO_2$, $P_2O_5$, $Al_2O_3$, and F in the case of passive fibers). In other embodiments, other suitable materials can be used for the cladding and the cores (e.g., plastic, sapphire, and composite glasses).

Each one of the cores 26a to 26d has a circular cross-section. However, a non-circular cross-section (e.g., elliptical) is possible in other embodiments. In some non-limiting embodiments, the cores 26a to 26d can have a diameter ranging from about 5 μm to about 30 μm, although other core sizes can be used in other embodiments. The core size can depend on various factors, for example the number of cores and the cross-sectional overall size of the multicore fiber 20. Each of the cores 26a to 26d can be either single mode or multimode. It is noted that multimode cores can generally provide better lateral coupling efficiency, which can be advantageous in scenarios where the optical power of the laterally coupled light is of importance.

Figure 3:
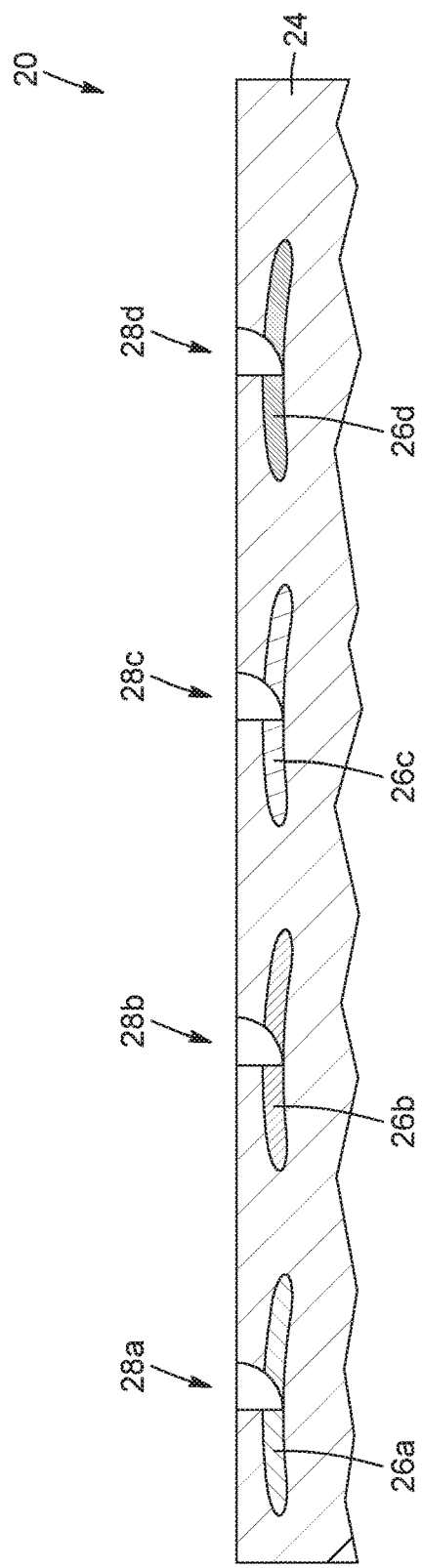
FIG. 3 is a longitudinal cross-sectional view of the multicore optical fiber of FIG. 1, taken along section line 3, depicting the longitudinal distribution of lateral coupling zones along the length of the fiber.
Figure 4A:
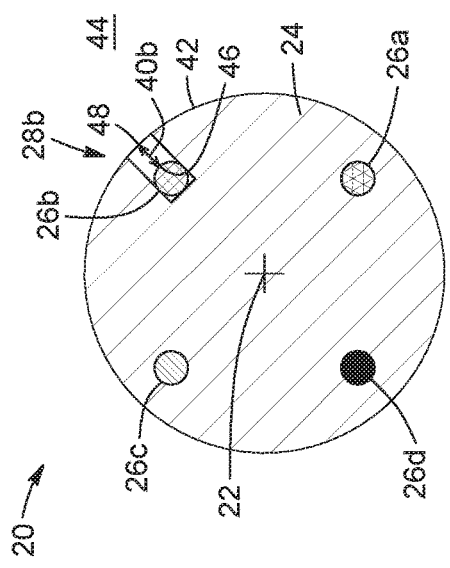
FIGS. 4A to 4D are transverse cross-sectional views of the multicore optical fiber of FIG. 1, taken along section lines 4A to 4D. Each one of FIGS. 4A to 4D depicts a different one of the longitudinally distributed lateral coupling zones.
Figure 4B:
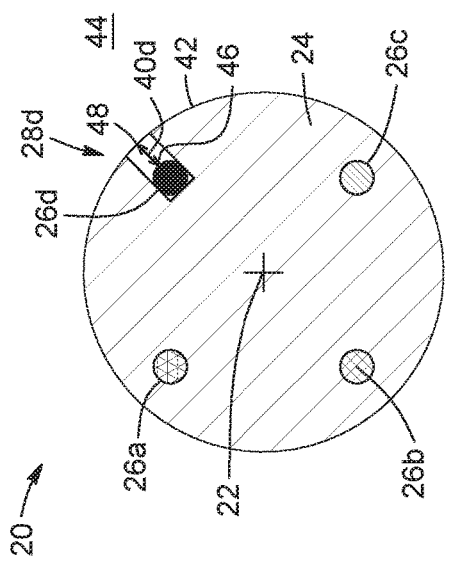
Figure 4C:
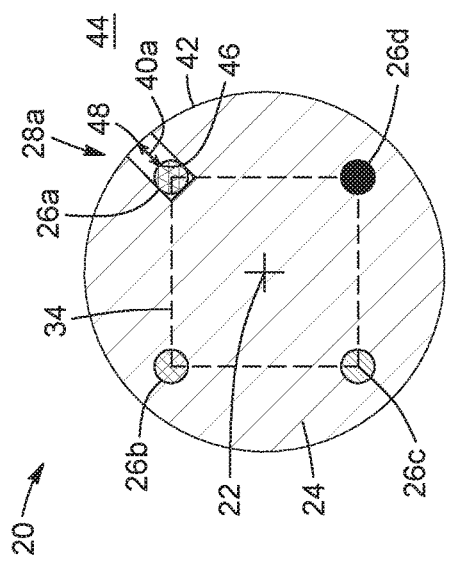
Figure 4D:
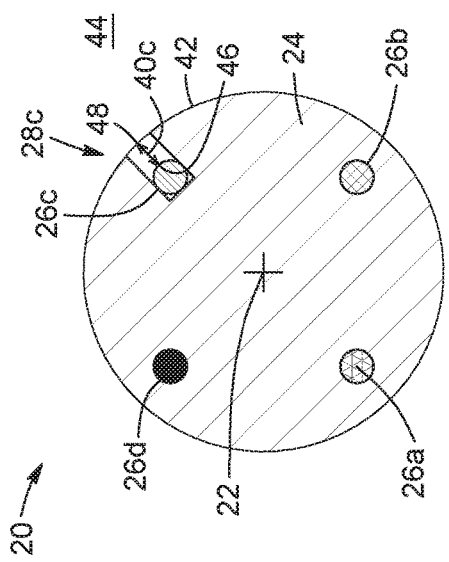

The arrangement of the cores 26a to 26d over the cross-section of the fiber 20 can assume various symmetrical or non-symmetrical configurations. For example, in some implementations, the cores 26a to 26d can be arranged, uniformly or not, along a perimeter of a closed-shape FIG. 34, as shown in FIG. 4A. The closed-shape FIG. 34 may or may not be centered with respect to the fiber axis 22. In some implementations, the closed-shape FIG. 34 may be a circle or another curved shape. In other implementations, the closed-shape FIG. 34 may be a polygon, regular or irregular, in which case the cores 26a to 26d can be located at vertices of the polygon. For example, in the embodiment of FIGS. 1 to 3 and 4A to 4D, the four cores 26a to 26d are located at the corners of a square centered on the fiber axis 22. In yet other implementations, the locations of the cores 26a to 26d can correspond to lattice points of an array or to arbitrary locations that do not conform to a specific pattern. It will be understood that the spacing between the cores 26a to 26d is generally sufficiently large to avoid excessive mutual inter-core coupling.

It is noted that depending on the application, the composition, cross-sectional shape and size, refractive index profile, number of guided modes, passive or active operation mode, polarization-maintaining properties and other core properties may be the same or differ among the different cores.

Figure 5:
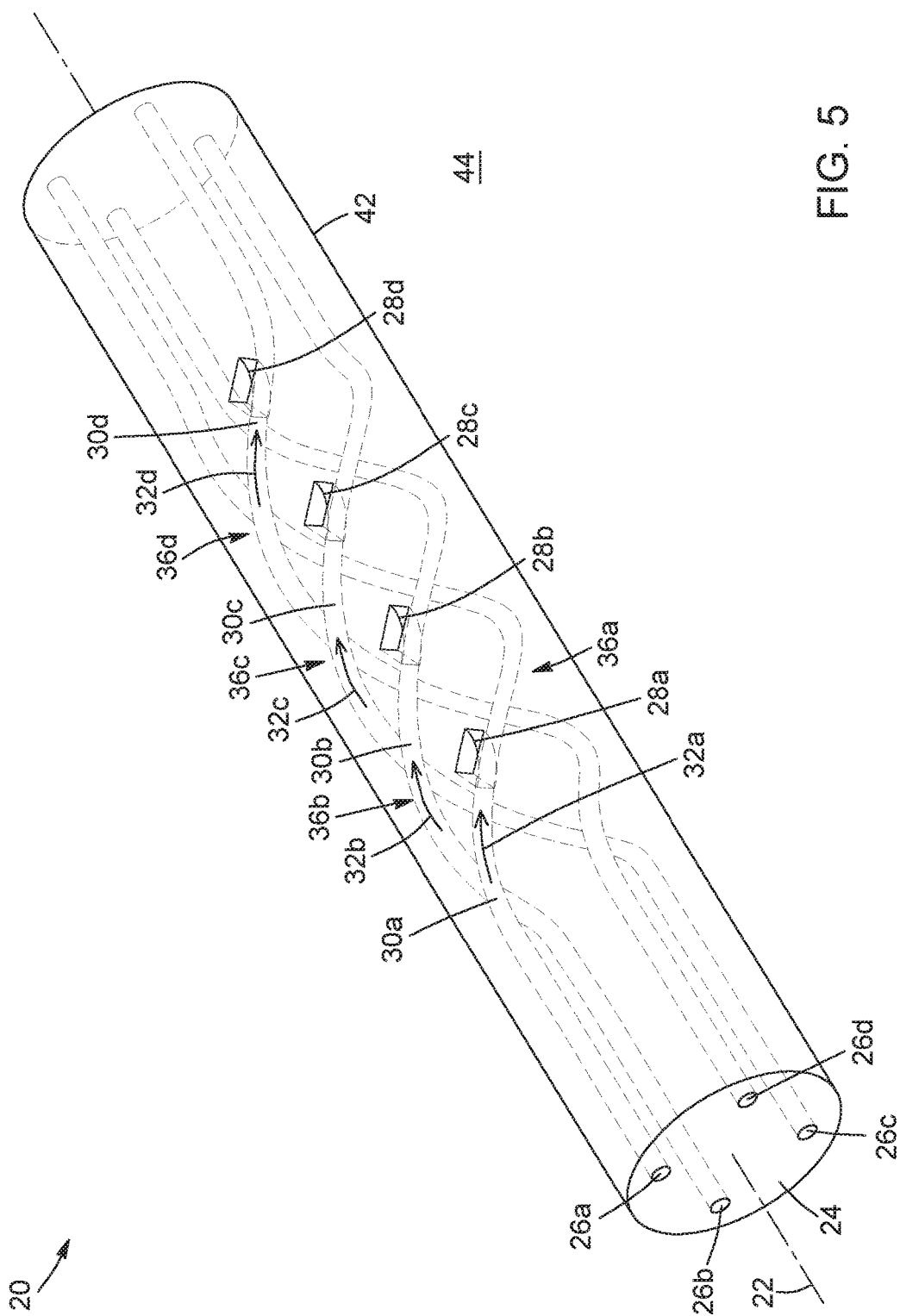
FIG. 5 is a schematic perspective view of a multicore optical fiber, in accordance with another exemplary embodiment, in which each one of the multiple cores follows a helical trajectory only along a partial length thereof. The cladding is shown as being transparent to better illustrate the helical trajectories followed by the multiple cores around the fiber axis.

Referring still to FIGS. 1 to 3 and 4A to 4D, the cores 26a to 26d follow respective helical trajectories 36a to 36d about the fiber axis 22. As shown more specifically in the transverse cross-sectional views of FIGS. 4A to 4D, as each core 26a to 26d travels along its respective helical trajectory 36a to 36d, the azimuthal angle it makes with respect to the fiber axis 22 gradually changes. Depending on the application, each core 26a to 26d can extend along its helical trajectory 36a to 36d along the entire length thereof, as illustrated in the embodiment of FIGS. 1 to 3 and 4A to 4D, or along a partial length thereof, as illustrated in the embodiment of FIG. 5.

The terms "helix", "helical", "helicoidal" and variants thereof refer to a three-dimensional figure that involves both a rotation around and a translation along a helix axis, which generally coincides with the fiber axis.

More particularly, the term "helical trajectory" is intended to describe the general configuration in which each one of the off-centered cores is wrapped or coiled around the fiber axis. It is noted that the terms "helix", "helical", "helicoidal" and variants thereof are not intended to be construed by their strictest geometrical definition and are meant to encompass both true helices (i.e., circular helices with a constant radius of curvature) and helix-like structures having a non-constant radius of curvature. Depending on the application, the helix can have a spatial repetition period and a helix angle which may be constant or vary along the helix axis.

Various techniques can be used to impart a helical configuration to the off-centered cores of the multicore fiber disclosed herein. In some implementations, the multicore fiber can have a permanent spin imparted thereto along the fiber axis. Such specialty optical fibers can be referred to as "spun fibers". It will be understood that by imparting a spin along a multicore fiber having multiple off-centered cores, a spun multicore fiber is obtained in which the off-centered cores rotate in a helical fashion about the fiber axis.

In the present description, the terms "spin", "spun" and other derivatives thereof are intended to refer to a torsional deformation which is impressed on the multicore fiber while the fiber material is in a viscous and substantially unstressed state, and which is preserved as a permanent structural modification after the fiber has cooled down. In this context, the term "permanent" is intended to refer to a deformation which is essentially non-reversible under normal operating conditions and for the intended lifetime of the multicore optical fiber.

In some implementations, a spun multicore fiber can be obtained during the drawing process, using either a preform spinning technique, in which the preform is rotated, or a fiber spinning technique, in which the fiber is rotated. In other implementations, a spun multicore fiber can be obtained by post-drawing processing.

Such processing can involve the following steps: performing a conventional drawing process to obtain an "unspun" multicore fiber, that is, a multicore fiber produced without spin; locally heating the unspun multicore fiber to bring at least a portion thereof to a soft and viscous state; applying a torque to the locally heated portion of the unspun fiber such that a spin is imparted to the locally heated portion and preserved as a frozen-in structural modification upon cooling. While the application of this technique is often restricted to a limited segment of a fiber, it can provide increased flexibility in terms of engineering the imparted spin properties.

In general, a spun optical fiber can be characterized by a spin function or profile.

In the present description, the term "spin function" is intended to refer to the rate (e.g., in units of degrees per unit length or turns per unit length) and direction (i.e., left-handed or right-handed) of the spin imparted to the fiber as a function of position along the fiber. The spin function may be of any kind, although spin functions with a constant rate are often favored. Moreover, the spin impressed on the fiber may have a constant handedness (i.e., a unidirectional spin function that is either everywhere left-handed or everywhere right-handed) along the fiber or may alternate, periodically or not, between a left-handed and a right-handed helicity.

The spin function can also be characterized by a spin pitch, or spatial repetition period. The spin pitch represents the length of fiber needed to complete a 360° rotation about the fiber axis. For example, in some implementations, the multicore optical fiber disclosed herein can have a spin pitch that ranges from about one centimeter to a few tens of centimeters or more (e.g., from about 5 mm to about 50 cm in a non-limiting embodiment). Of course, other spin pitch values can be used in other embodiments. Depending on the application, the spin pitch may be constant or vary, periodically or not, as a function of the position along the fiber axis, and different cores may have the same or different spin pitch values. More detail regarding the spin pitch and how its value can be used to control the longitudinal spacing between the lateral coupling zones of the multicore fiber will be described further below.

It should be noted that the terms "spin" and "twist" are employed in the art to describe two distinct types of rotation or torsion that can be impressed on a fiber. This distinction will be adopted in the present description. As defined above, the term "spin" refers to a rotation applied to the fiber in a way that produces a substantially permanent deformation after cooling. In contrast, the term "twist" refers to an elastic rotation applied to a post-drawn fiber in a way such that the fiber will return to its original state after removing the torsional torque. Depending on the application, the multicore fiber disclosed herein may be either spun or twisted. In some implementations, spun fibers can be favored compared to twisted fibers due to their mechanical stability, resistance to long-term fatigue, and manufacturing flexibility that can allow short and/or longitudinally varying spatial repetition periods.

Figure 6:
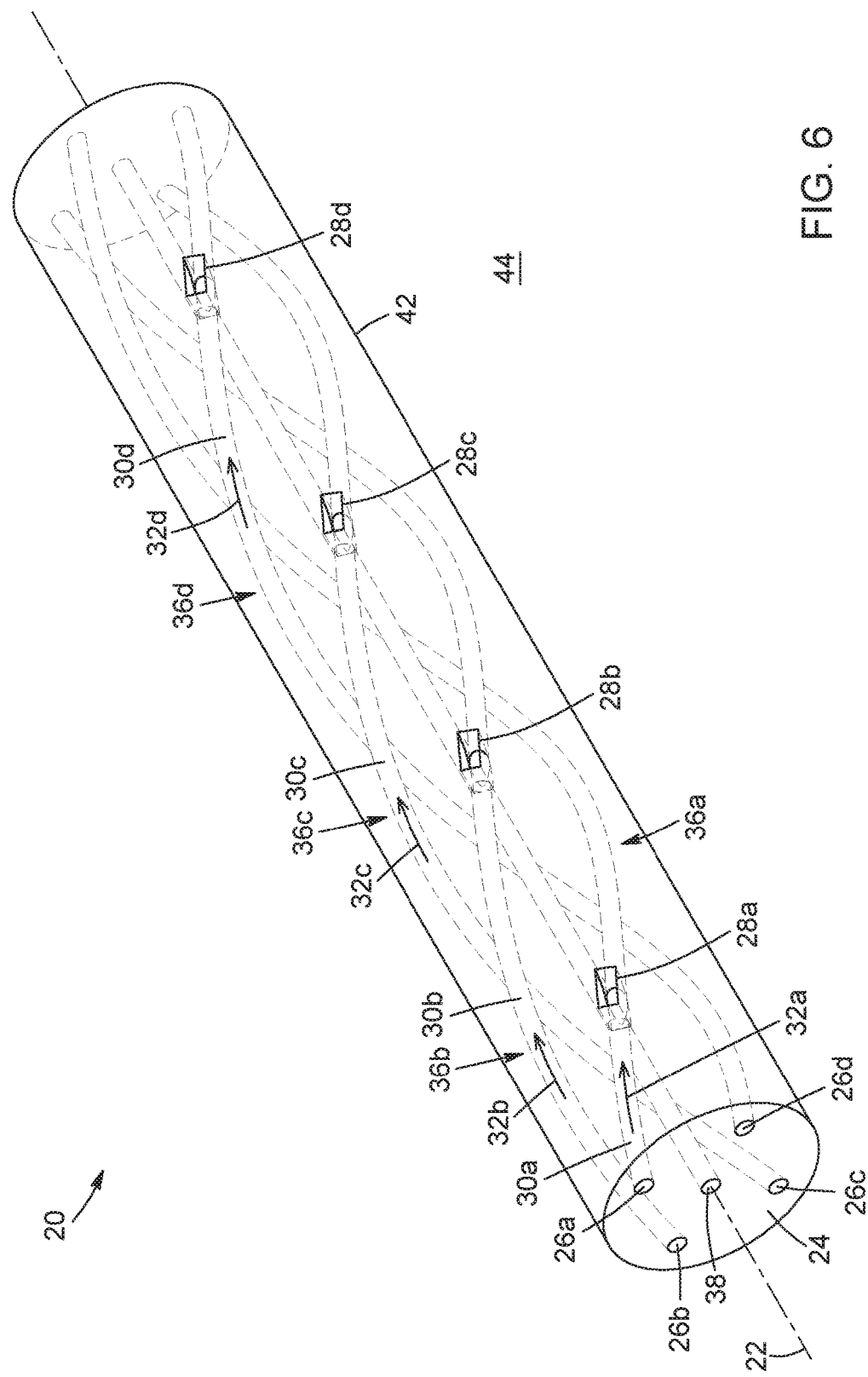
FIG. 6 is a schematic perspective view of a multicore optical fiber, in accordance with another exemplary embodiment, in which the multicore optical fiber includes multiple off-centered cores extending helically about a centered core coaxially aligned with the fiber axis. The cladding is shown as being transparent to better illustrate the helical trajectories followed by the multiple cores around the fiber axis.

Turning briefly to FIG. 6, it should be noted that if the multicore optical fiber 20 also includes a centered core 38, in addition to the multiple off-centered cores 26a to 26d, the centered core 38 would not follow a helical path, but would remain generally straight and coaxially aligned with the fiber axis 22.

Returning to the embodiment of FIGS. 1 to 3 and 4A to 4D, the multicore optical fiber 20 includes a set of lateral coupling zones 28a to 28d. The lateral coupling zones 28a to 28d are longitudinally spaced-apart from and azimuthally aligned with one another relative to the fiber axis 22. Each one of the lateral coupling zones 28a to 28d forms an optical coupling path or optical channel 40a to 40d that extends between a corresponding one of the cores 26a to 26d and an outer lateral surface 42 of the multicore fiber 20, and that enables coupling of light between the corresponding core 26a to 26d and the exterior 44 of the fiber 20.

In the present description, the term "lateral coupling zone" generally refers to a zone in the multicore fiber in which optical energy can travel or be coupled between one of the cores and a location outside of the multicore fiber. For brevity, the term "lateral coupling zone" may, in some instances, be shortened to "coupling zone". Depending on the application, the lateral coupling zones can provide both unidirectional and bidirectional optical coupling, and be configured to transmit all or a portion of the light received therein, in either direction. In some implementations, the coupling efficiency can be spectrally dependent. Also, depending on the application, the lateral coupling zones can enable optical coupling to be effected either by direct optical coupling (see, e.g., FIGS. 8 to 12) or by evanescent wave coupling (see, e.g., FIG. 13).

In the present description, the term "lateral" when referring to the lateral coupling zones is intended to refer to the fact that light coupling between the corresponding core and the exterior of the fiber is effected through the outer lateral surface of the multicore fiber, rather than, for example, through a fiber endface. It is noted that the term "lateral coupling" may, in some instances, be used interchangeably with the terms "radial coupling" and "side coupling".

When referring to the spatial arrangement of the set of lateral coupling zones, the term "longitudinally distributed" is intended to refer herein to the fact that the set of lateral coupling zones is arranged in a manner such that the individual coupling zones are disposed, formed or otherwise provided at discrete, spaced-apart locations along the length of the fiber. By way of example, the longitudinal cross-sectional view of FIG. 3 shows the spaced-apart distribution of the lateral coupling zones 28a to 28d along the fiber axis 22. It will be understood that such longitudinally distributed coupling zones 28a to 28d can provide multipoint quasi-distributed sensing and probing along the fiber axis 22.

When referring to the spatial arrangement of the set of lateral coupling zones, the term "azimuthally aligned" is intended to refer herein to the fact that all the lateral coupling zones in the set are located at the same azimuthal position or angle in the multicore fiber, the azimuthal position or angle being defined relative to the fiber axis. The term "azimuthally aligned" is also intended to refer to the fact that all the lateral coupling zones in the set are provided in a common azimuthal plane or within a common azimuthal angular range with respect to the fiber axis. By way of example, referring to the transverse cross-sectional views of FIGS. 4A to 4D, it is seen that the four lateral coupling zones 28a to 28d are all formed at the same azimuthal position (at 1:30 o'clock position in the figures) around the fiber axis 22.

It is noted that a set of longitudinally distributed lateral coupling zones provided at the same azimuth in the multicore fiber can be referred to as a "linear array of longitudinally distributed lateral coupling zones". It is also noted that the terms "azimuthal" and "azimuthally aligned" may, in some instances, be used interchangeably with the terms "circumferential" and "circumferentially aligned", respectively.

In some implementations, using a set of longitudinally distributed and azimuthally aligned lateral coupling zones for enabling multipoint quasi-distributed light injection to and/or light collection from a multicore optical fiber with a helical core arrangement can be advantageous for applications in space-confined and other restricted environments where multipoint sensing and probing over an azimuthally narrow range of angles is required or desired. The fact the lateral coupling zones are all provided on the same optical fiber can also be an advantage in terms of compactness and design simplicity in spatially restricted environments.

Referring to FIGS. 4A to 4D, the optical coupling path 40a to 40d of each lateral coupling zone 28a to 28b is the path or channel along which lateral optical coupling is effected between the corresponding core 26a to 26d and the exterior 44 of the fiber 20. Each optical coupling path 40a to 40d has an inner end 46 and an outer end 48. The inner end 46 is located at a point along the helical trajectory followed by the core 26a to 26d, while the outer end 48 is located at a point on the outer lateral surface 42 of the fiber 20. It should be noted that the optical coupling path 40a to 40d of each lateral coupling zone 28a to 28d need not extend solely in a lateral direction with respect to the fiber axis 22, but may exhibit a slight longitudinal deviation or slope as it extends between its inner end 46 and its outer end 48.

Referring to FIGS. 1 to 3 and 4A to 4D, in some implementations, one, some, or all of the lateral coupling zones 28a to 28d can enable bidirectional coupling of light between the cores 26a to 26d and the exterior 44 of the fiber 20. This or these coupling zones 28a to 28d allow both in-coupling and out-coupling of light to and from the cores 26a to 26d via the set of discrete, longitudinally distributed lateral coupling zones 28a to 28d. In such implementations, the multicore optical fiber 20 can be used in applications requiring multipoint quasi-distributed light delivery and collection.

In some implementations, one, some, or all of the lateral coupling zones 28a to 28d can enable light to be transmitted from the cores 26a to 26d to the exterior 44 of the fiber 20. This or these coupling zones 28a to 28d allow light to escape or be out-coupled from the cores 26a to 26d. In such implementations, the multicore optical fiber 20 can be used in multipoint quasi-distributed light delivery applications, in which guided light 32 is coupled out the multiple cores 26a to 26d via the set of discrete, longitudinally distributed lateral coupling zones 28a to 28d. For example, in FIG. 17, all the cores 26a to 26d are used for unidirectional light delivery.

In some implementations, one, some, or all of the lateral coupling zones 28a to 28d can enable light to be received from the exterior 44 to the cores 26a to 26d of the fiber 20. This or these coupling zones 28a to 28d allow light to be injected in or be in-coupled to the cores 26a to 26d. In such implementations, the multicore optical fiber 20 can be used in multipoint quasi-distributed light collection applications, in which incoming light from a region of interest is coupled into the multiple cores 26a to 26d via the set of discrete, longitudinally distributed lateral coupling zones 28a to 28d.

Figure 18:
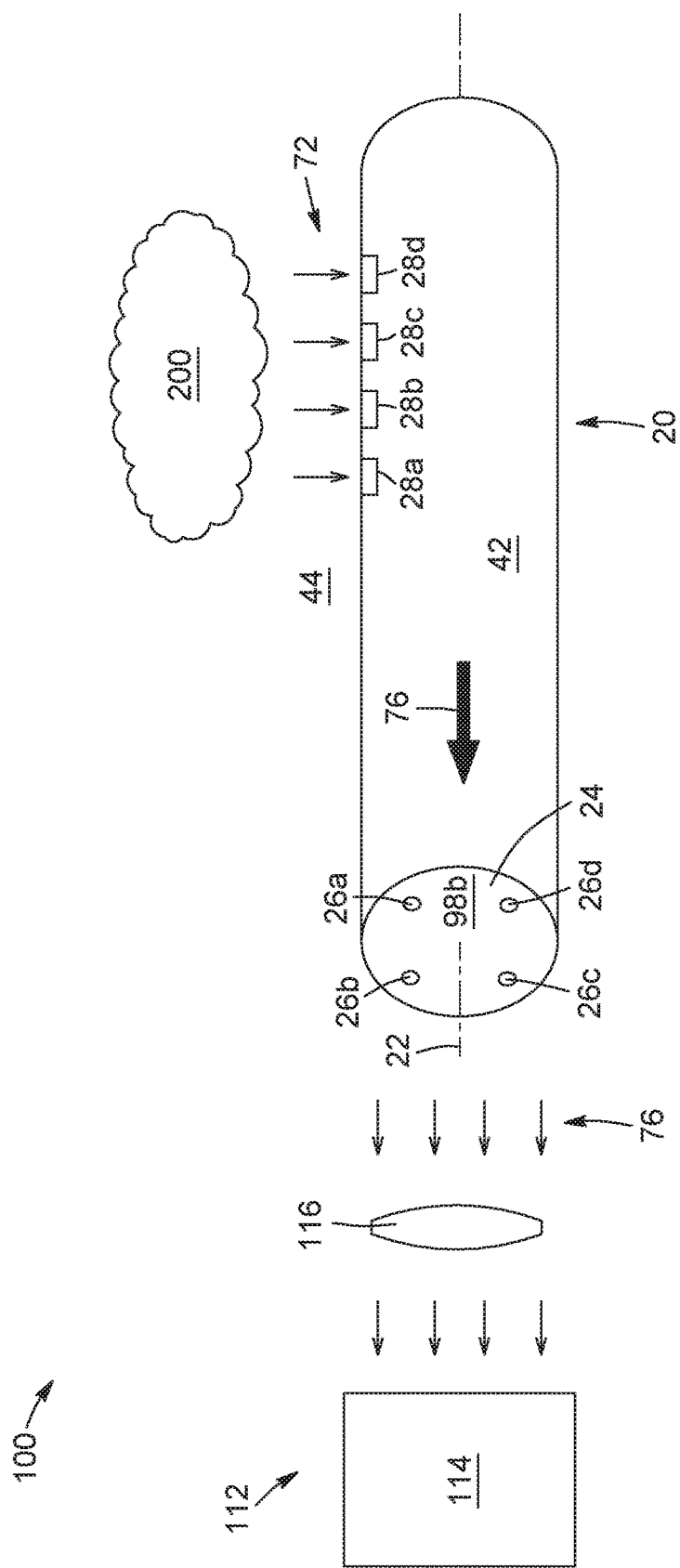
FIG. 18 is a schematic representation of an optical probing system for light collection, in accordance with another embodiment, in which all the lateral coupling zones are used only for light collection.

For example, in FIG. 18, all the cores 26a to 26d are used for unidirectional light collection.

Therefore, depending on the application or use of the multicore optical fiber, each lateral coupling zone can therefore provide one of the following types of optical coupling: unidirectional coupling of light from the corresponding core to the exterior of the fiber (i.e., unidirectional coupling for light delivery); unidirectional coupling of light from the exterior of the fiber to the corresponding core (i.e., unidirectional coupling for light collection); and coupling of light from the corresponding core to the exterior of the fiber, and vice versa (i.e., bidirectional coupling for simultaneous light delivery and collection). Lateral coupling zones with different configurations can be used to provide different types of optical coupling. By way of example, in some implementations, each coupling zone can be configured to couple light in a specific spectral range selected in accordance with the wavelength(s) of the light traveling in the corresponding core.

Returning to FIGS. 1 to 3 and 4A to 4D, in some implementations, the distance between adjacent coupling zones 28a to 28d can range from a few hundreds of micrometers to a few centimeters, and in some implementations from 1 mm to 10 mm. Depending on the application, the lateral coupling zones 28a to 28d can be uniformly spaced-part, as in FIGS. 1 to 3 and 4A to 4D, or nonuniformly spaced-apart.

Figure 7:
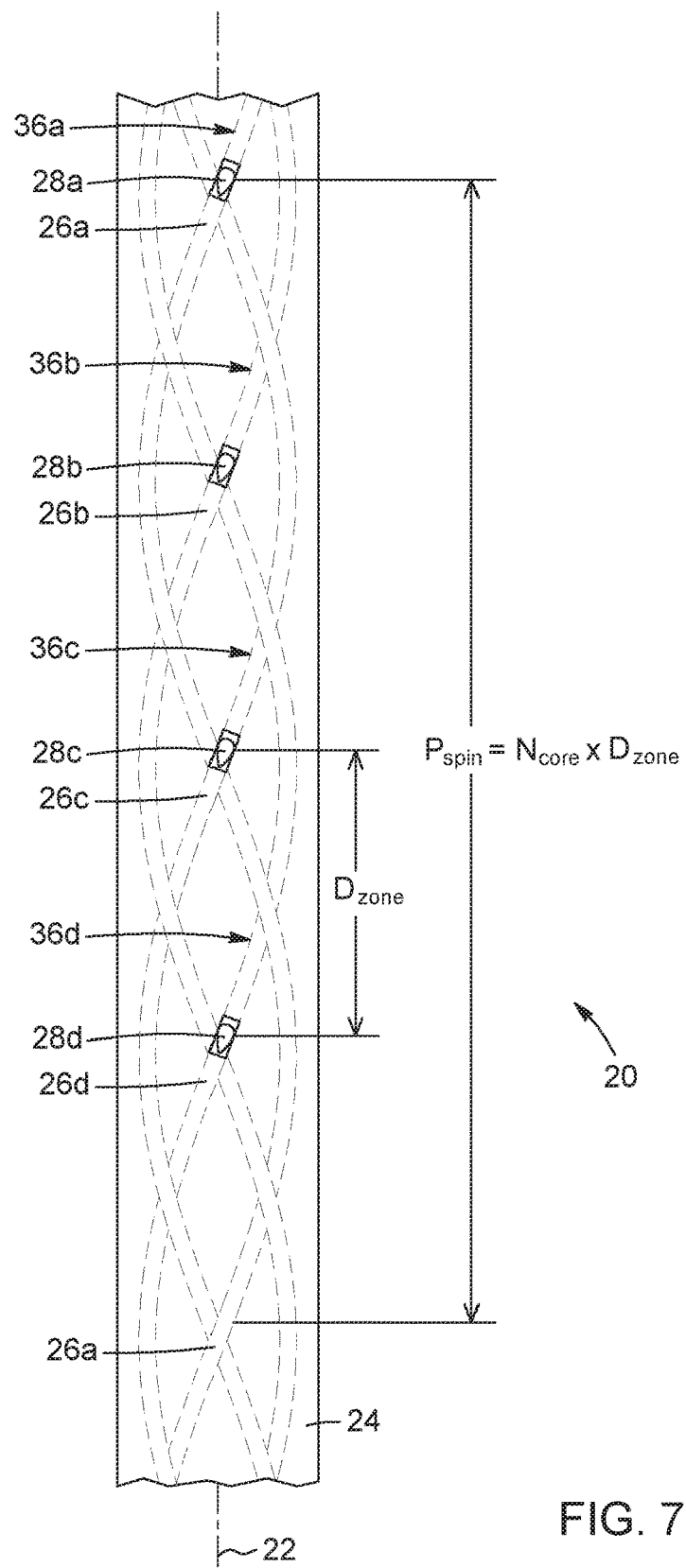
FIG. 7 is a schematic plan view of a multicore optical fiber, in accordance with another exemplary embodiment, illustrating the helical trajectories followed by the cores and the arrangement of the lateral coupling zones.

Referring to FIG. 7, the minimum achievable distance $D_{zone}$ between adjacent coupling zones 28a to 28d is generally related to the number $N_{core}$ of helically arranged cores 26a to 26d and the spin pitch $P_{spin}$ of their helical trajectories 36a to 36d, as follows: $P_{spin} = N_{core} \times D_{zone}$. As mentioned above, the multicore fiber 20 may include between 2 and 50 cores, and the spin pitch $P_{spin}$ can be as short as 5 mm. Therefore, using for example $N_{core} = 20$ and $P_{spin} = 5$ mm, the distance $D_{zone}$ between adjacent coupling zones 28a to 28d can be as small as 250 µm. Such small values can be advantageous for multipoint quasi-distributed sensing and probing applications where spatial resolution is of importance, especially considering that the lateral coupling zones are not only longitudinally distributed, but also azimuthally aligned. This azimuthal alignment allows light delivery and/collection to be confined within a narrow range of azimuthal angles.

It will be understood that in the exemplary embodiments described so far, the lateral coupling zones are arranged in a "close-packed" configuration, in which the longitudinal distance between adjacent coupling zones is equal to the longitudinal offset between the helical trajectories of adjacent cores. Of course, in other embodiments, the lateral coupling zones can be arranged into more complex configurations in terms of order and mutual separations provided that they remain in a longitudinally distributed and azimuthally aligned arrangement with respect to the fiber axis.

It will also be understood that in the exemplary embodiments described so far, only a single set of longitudinally distributed and azimuthally aligned lateral coupling zones was considered, in which the number of coupling zones was equal to the number of multiple cores. However, in other variants the multicore fiber can include a plurality of sets of longitudinally distributed and azimuthally aligned lateral coupling zones. For example, in some embodiments, the different sets can be longitudinally spaced-apart from one another, but they may or may not be azimuthally aligned with one another. It is noted that depending on the application, the number of coupling zones in each set can be less or greater than the number of cores in the multicore fiber, provided that, in any given set, the coupling zones remain in a longitudinally distributed and azimuthally aligned arrangement with respect to the fiber axis.

It will therefore be understood that depending on the application or use of the multicore optical fiber, the lateral coupling zones can have a variety of structures, configurations, and operation principles, which may be the same or different for each lateral coupling zone. Several non-limiting examples of implementations for the lateral coupling zones will now be described with reference to FIGS. 8 to 13.

It is noted that, unless explicitly stated otherwise, each of these exemplary implementations are reciprocal, which means that they enable light to be coupled laterally from the core to the exterior of the fiber as readily as they do from the exterior to the core of the fiber. It is also noted that each of the exemplary implementations illustrated in FIGS. 8 to 13 will be described by considering a single lateral coupling zone 28 forming an optical coupling path 40 that enables lateral coupling of light between a corresponding core 26 and the exterior 44 of a multicore fiber 20. As mentioned above, the corresponding core 26 is disposed in a cladding 24 and has a light-guiding path 30 that follows a helical trajectory 36 about the fiber axis 22. However, it will be understood that each of these examples can be used for one, some, or all of the lateral coupling zones of the fiber. It is further noted that other non-limiting examples of lateral coupling arrangements that may be suitable for implementing the lateral coupling zones disclosed herein are described in co-assigned U.S. Pat. Nos. 7,209,605 and 7,883,535, the disclosures of which are incorporated herein by reference in their entirety.

Figure 8:
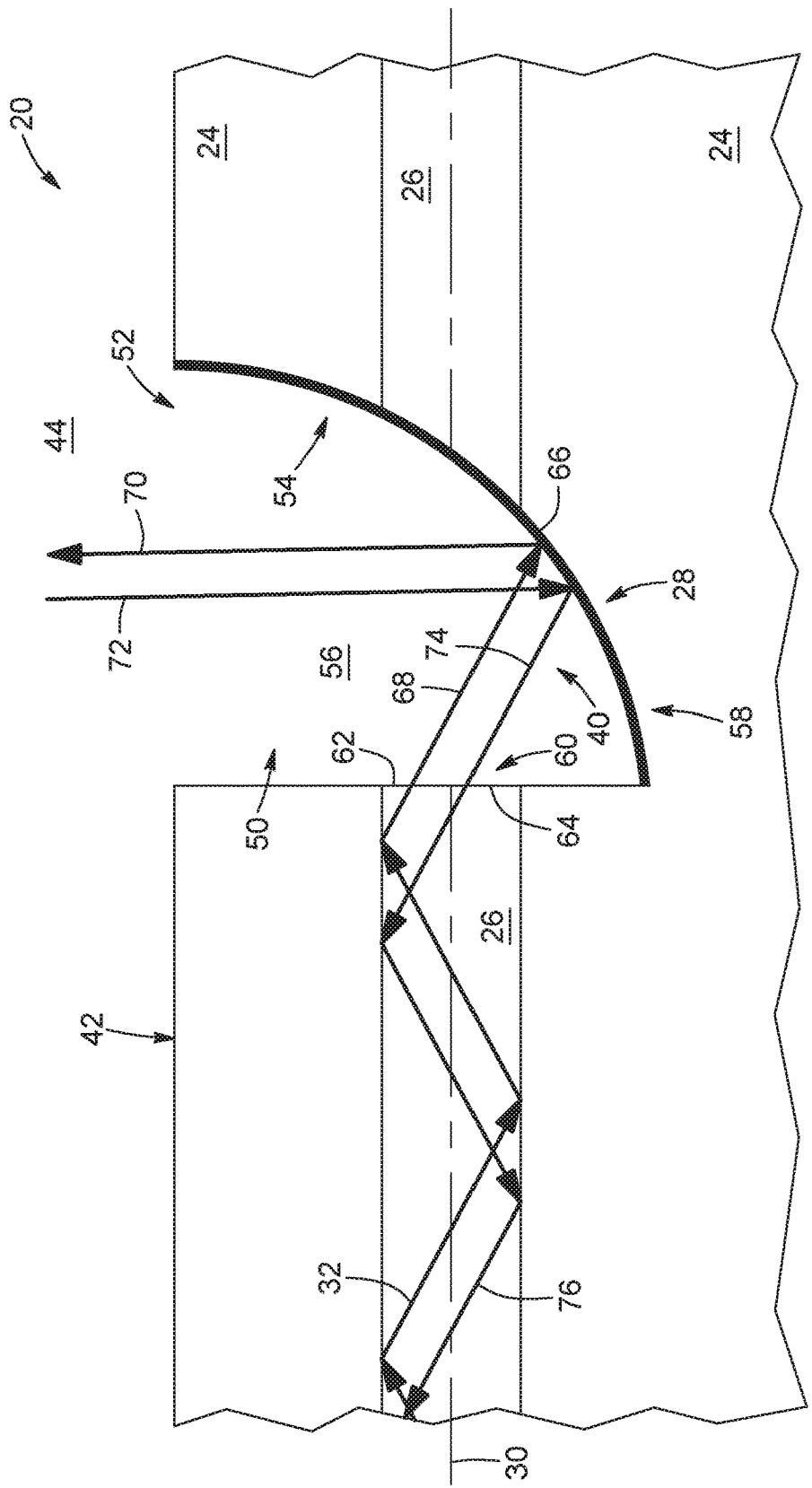
FIG. 8 is a schematic longitudinal cross-sectional view of a lateral coupling zone of a multicore optical fiber, in accordance with a first variant, in which the lateral coupling zone includes a cavity and a curved light reflector deposited inside the cavity.

Referring to FIG. 8, there is shown a first exemplary implementation of a lateral coupling zone 28 of a multicore optical fiber 20. In this implementation, the lateral coupling zone 28 includes a cavity 50 formed by removing part of the cladding 24 and the core 26. The cavity 50 extends inwardly from the outer lateral surface 42 of the fiber 20 into the cladding 24 and at least partly into the core 26. By way of example, in the illustrated embodiment, the cavity 50 extends through and beyond the core 26 to terminate in the cladding 24. The cavity 50 has a cavity opening 52 defined through the outer lateral surface 42 of the fiber 20 and a cavity wall 54 extending from the cavity opening 52 and defining a cavity interior 56 terminating in a closed bottom 58. The cavity 50 has a limited extent both longitudinally (e.g., between about 50 µm and about 100 µm) and azimuthally (e.g., between about 50 µm and about 100 µm) over the outer lateral surface 42 of the fiber 20. The size of the cavity 50 can be determined based on the application requirements, for example in terms of spatial resolution and/or sensitivity. The cavity wall 54 has a portion thereof that defines an optical interface 60 between the cavity interior 56, on a cavity side 62 of the interface 60, and the core 26, on a core side 64 of the interface 60.

The cavity 50 can be formed by laser processing (e.g., laser ablation and laser cutting), chemical or physical etching, mechanical techniques (e.g., drilling, cutting, and milling), or any other appropriate micromachining technique. By way of example, in some implementations, the cavity 50 can be formed by laser ablation, such as femtosecond or $CO_2$ laser ablation. As known in the art, laser ablation can be used to precisely and accurately form cavities having complex and/or irregular shapes, ranging in size from about a few tens of micrometers to about a few hundred of micrometers.

Depending on the application, the cavity 50 may be hollow or be filled at least partly with a filling material. Several techniques exist for inserting a filling material inside a cavity and they need not be discussed in detail herein. In some implementations, inserting a filling material inside the cavity can help mitigating Fresnel reflections at the optical interface 60 between the core 26 and the cavity interior 56.

It will be understood that depending on the application, the coupling efficiency provided by the lateral coupling zone 28 can be optimized by proper selection of the size and shape of the cavity 50 and, if any, of the optical property of the filling material, notably its refractive index relative to the refractive indices of the core 26 and the cladding 24. For example, in the embodiment of FIG. 8, the cavity 50 is hollow (i.e., filled with air) and is shaped as a half paraboloid. Of course, depending on the application, various other regular or irregular cavity shapes can be used. It is noted that the term "cavity" can be used interchangeably herein with terms such as "groove", "depression", "hole", "recess", "aperture", and the like.

In some implementations, the lateral coupling zone 28 can include a light reflector 66 located inside the cavity 50 along the optical coupling path 40. In the present description, the term "light reflector" refers to an optical element or a combination of optical elements which can reflect, at least partly, the light incident thereonto. In some implementations, the light reflector 66 can be a reflective layer deposited over a portion of the cavity wall 54. For example, the reflective layer can be embodied by a metallic mirror (e.g., a thin metallic layer or film) or a dielectric mirror (e.g., a stack of dielectric thin films). Depending on the application, the light reflector 66 can be plane or curved. By way of example, in the illustrated embodiment, the light reflector 66 is embodied by a half paraboloidal reflector, but other light reflector shapes can be used in other embodiments.

Referring still to FIG. 8, the light reflector 66 can be disposed on the cavity wall 54 such that the optical coupling path 40 formed by the lateral coupling zone 28 includes both a reflection off the light reflector 66 on the cavity side 62 of the optical interface 60 and a transmission across the optical interface 60 between the core side 64 and the cavity side 62. Depending on whether light is coupled out of or into the core 26, the transmission will precede or follow the reflection along the optical coupling path 40.

In the out-coupling direction, guided light 32 propagating in the core 26 toward the cavity 50 will be transmitted across the optical interface 60 and into the cavity 50. Inside the cavity 50, the transmitted light 68 will impinge on and be reflected by the light reflector 66 toward the cavity opening 52 and out of the fiber 20 as outcoming light 70. Meanwhile, in the in-coupling direction, incoming light 72 passing through the cavity opening 52 will impinge on and be reflected by the light reflector 66 toward the optical interface 60. The reflected light 74 will then be transmitted across the optical interface 60 and into the core 26, inside which it will propagate as collected light 76 away from the cavity 50.

Figure 9:
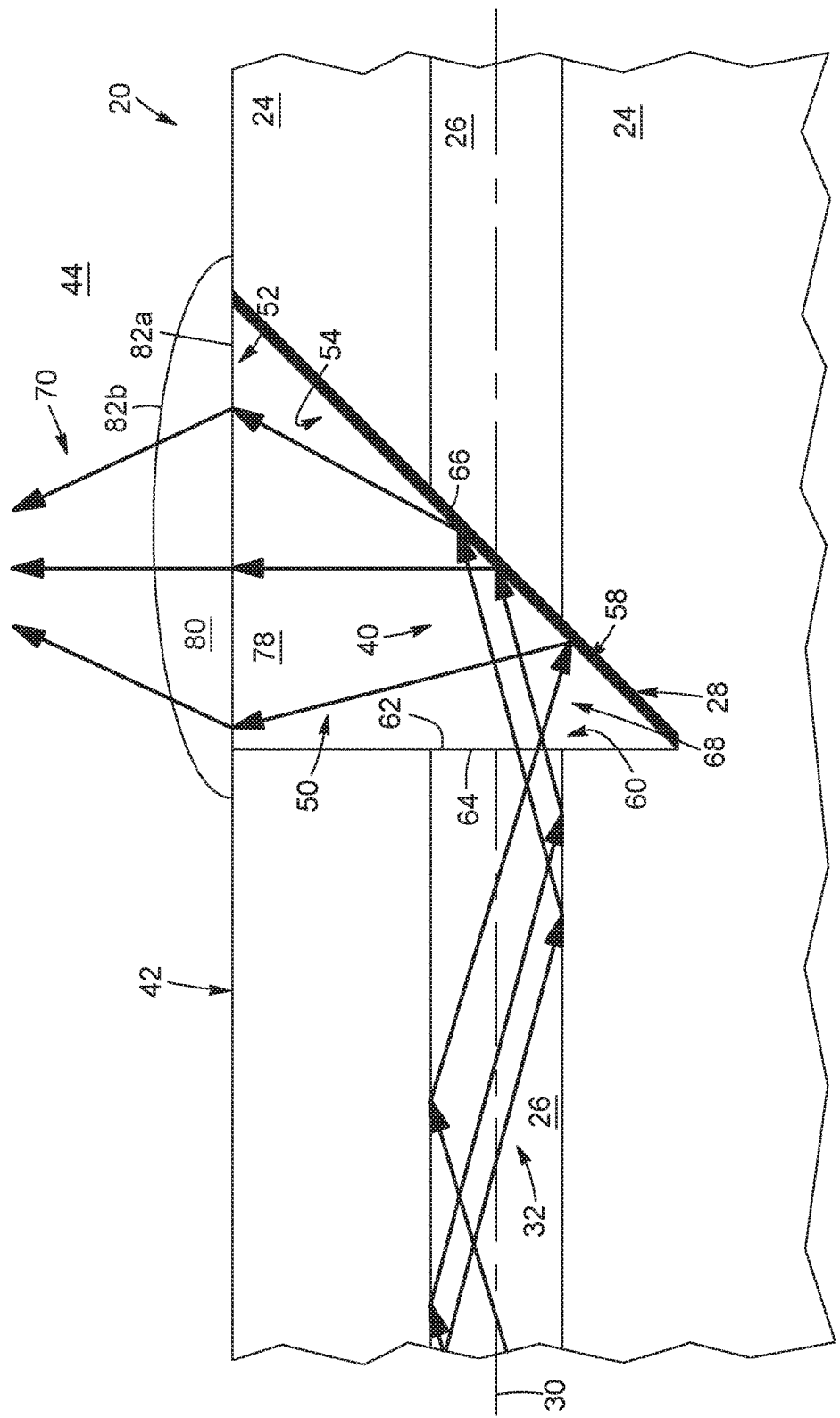
FIG. 9 is a schematic longitudinal cross-sectional view of a lateral coupling zone of a multicore optical fiber, in accordance with a second variant, in which the lateral coupling zone includes a cavity and a plane light reflector deposited on the cavity.

Referring now to FIG. 9, another exemplary implementation of a lateral coupling zone 28 is shown. The features of this implementation are generally similar to like features described for the implementation of FIG. 8, and they will not be repeated in detail below except for highlighting differences. The lateral coupling zone 28 of FIG. 9 differs from that of FIG. 8 in that the cavity 50 is shaped as a triangular prism rather than as a half paraboloid, such that the light reflector 66 is a plane reflector rather than a curved one. Also, the cavity 50 in FIG. 9 is filled with a filling material 78.

The lateral coupling zone 28 in FIG. 9 includes focusing optics 80 extending across the opening 52 of the cavity 50 to increase the coupling efficiency of light in and out of the fiber 20. For example, in the illustrated embodiment, the focusing optics 80 is embodied by a plano-convex lens having a flat side 82a facing the cavity 50 and a curved side 82b facing the exterior 44 of the fiber 20. In such a configuration, the provision of a plano-convex lens can allow the out-coupled light 70 to exit the cavity 50 as a focusing or converging beam of light. It is noted that while FIG. 9 only shows light being coupled from the core 26 to the exterior 44 of the fiber 20, this implementation could also enable light coupling from the exterior 44 of the fiber 20 to the core 26.

Figure 10:
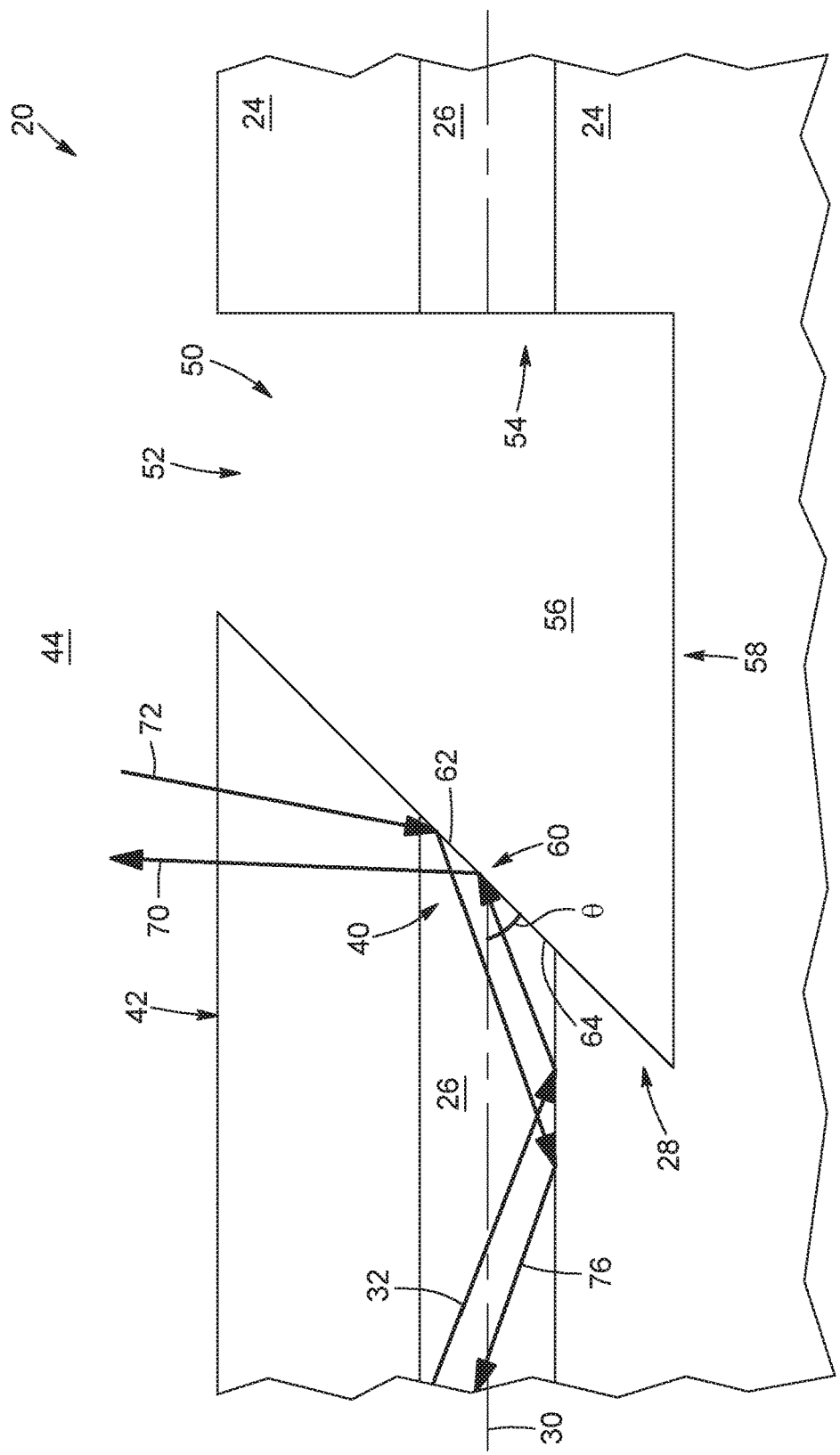
FIG. 10 is a schematic longitudinal cross-sectional view of a lateral coupling zone of a multicore optical fiber, in accordance with a third variant, in which the lateral coupling zone includes a cavity forming an optical interface with the core and enabling coupling of light by total internal reflection of light upon the core side of the optical interface.

Turning now to FIG. 10, another exemplary implementation of a lateral coupling zone 28 is shown. The implementation shown in FIG. 10 differs from the implementations shown in FIGS. 8 and 9 in the principle according to which light is laterally coupled by the cavity 50 between the core 26 and the exterior 44 of the fiber 20. In contrast to the implementations of FIGS. 8 and 9, the cavity 50 in the implementation of FIG. 10 does not include a light reflector and is also not traversed by the optical coupling path 40 between the core 26 and the exterior 44 of the fiber 20. Instead, the cavity 50 in FIG. 10 is shaped such that the optical interface 60 between the core 26 and the cavity interior 56 where light is coupled from and/or to the core 26 makes an angle $\theta$ with respect to the light-guiding path 30 of the core 26 that provides total internal reflection of light from the core side 64 of the interface 60.

As such, the optical coupling path 40 formed by the lateral coupling zone 28 includes a total internal reflection of light on the core side 64 of the optical interface 60, but no transmission across the interface 60. More particularly, this means that in the out-coupling direction, guided light 32 propagating in the core 26 toward the cavity 50 will undergo total internal reflection at the optical interface 60 and be coupled out of the fiber 20 as outcoming or delivered light 70. Similarly, in the in-coupling direction, incoming light 72 from the exterior 44 of the fiber 20 will traverse the cladding 24, undergo total internal reflection at the optical interface 60, and be coupled into the core for propagation therealong as collected light 76. In some variants, a filling material (not shown) may be inserted inside the cavity 50, if required to achieve total internal reflection. It is noted that forming the cavity 50 with a shape such as that shown in FIG. 10 is readily possible using conventional micromachining techniques. It is also noted that the implementation of FIG. 10 can be advantageous in terms of manufacturing cost, since no light reflector needs to be deposited inside the cavity.

Figure 11:
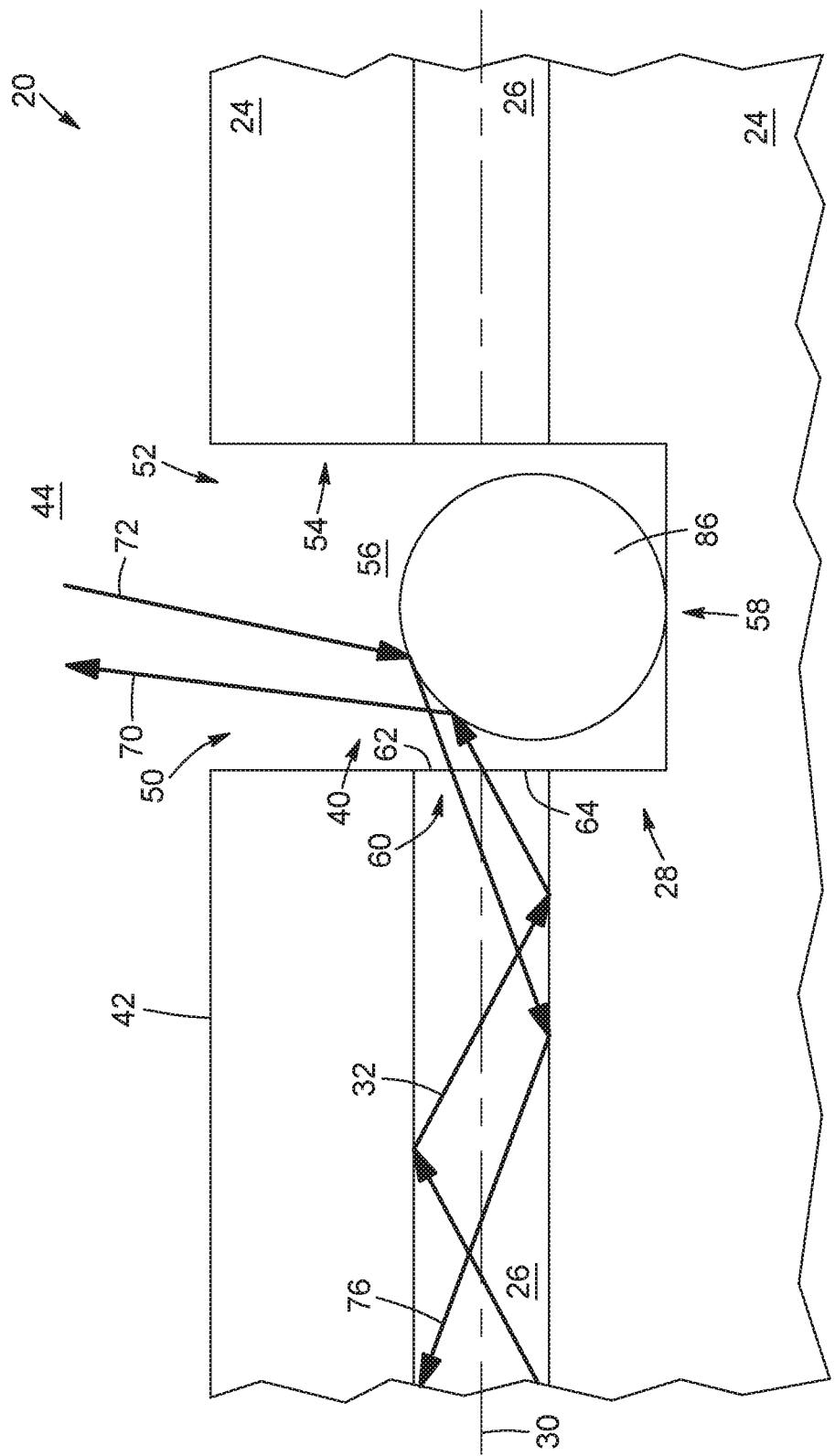
FIG. 11 is a schematic longitudinal cross-sectional view of a lateral coupling zone of a multicore optical fiber, in accordance with a fourth variant, in which the lateral coupling zone includes a cavity and a light reflector embodied by a reflective microsphere located inside the cavity.

Referring to FIG. 11, in another embodiment, the lateral coupling zone 28 can include a cavity 50 such as described above and a light reflector embodied by a reflective microsphere 86 located inside the cavity 50. In this embodiment, lateral optical coupling between the core 26 and the exterior 44 of the fiber 20 is effected by reflection of light on the reflective microsphere 86, as illustrated in FIG. 11. The reflective microsphere 86 may be glued or otherwise held in place inside the cavity 50. In other variants, the reflective microsphere 86 may be replaced with a similar reflective structure, such as, for example, a bead or a micro-prism.

Each one of the embodiments of FIGS. 8 to 11 includes lateral coupling zones embodied by longitudinally distributed and azimuthally aligned cavities formed by removing material from the outer lateral surface of the multicore fiber 20. The spacing between such cavities can be of the order of a few hundreds of micrometers using existing spinning and micromachining techniques, which may be advantageous in applications where high spatial resolution is desired or required. It is noted that such high spatial resolution may not be readily achievable using other implementations of lateral optical coupling zones disclosed herein, such as lateral coupling zones based on tilted or slanted fiber Bragg gratings (see, e.g., the embodiment described below and illustrated in FIG. 12), for which a minimum grating length may be required to yield acceptable coupling efficiency. Moreover, in contrast to most implementations based on fiber Bragg gratings, implementations using lateral coupling zones based on cavities such as those shown in FIGS. 8 to 11 need not work on a principle of resonance, which can allow a more stable and robust operation.

Figure 12:
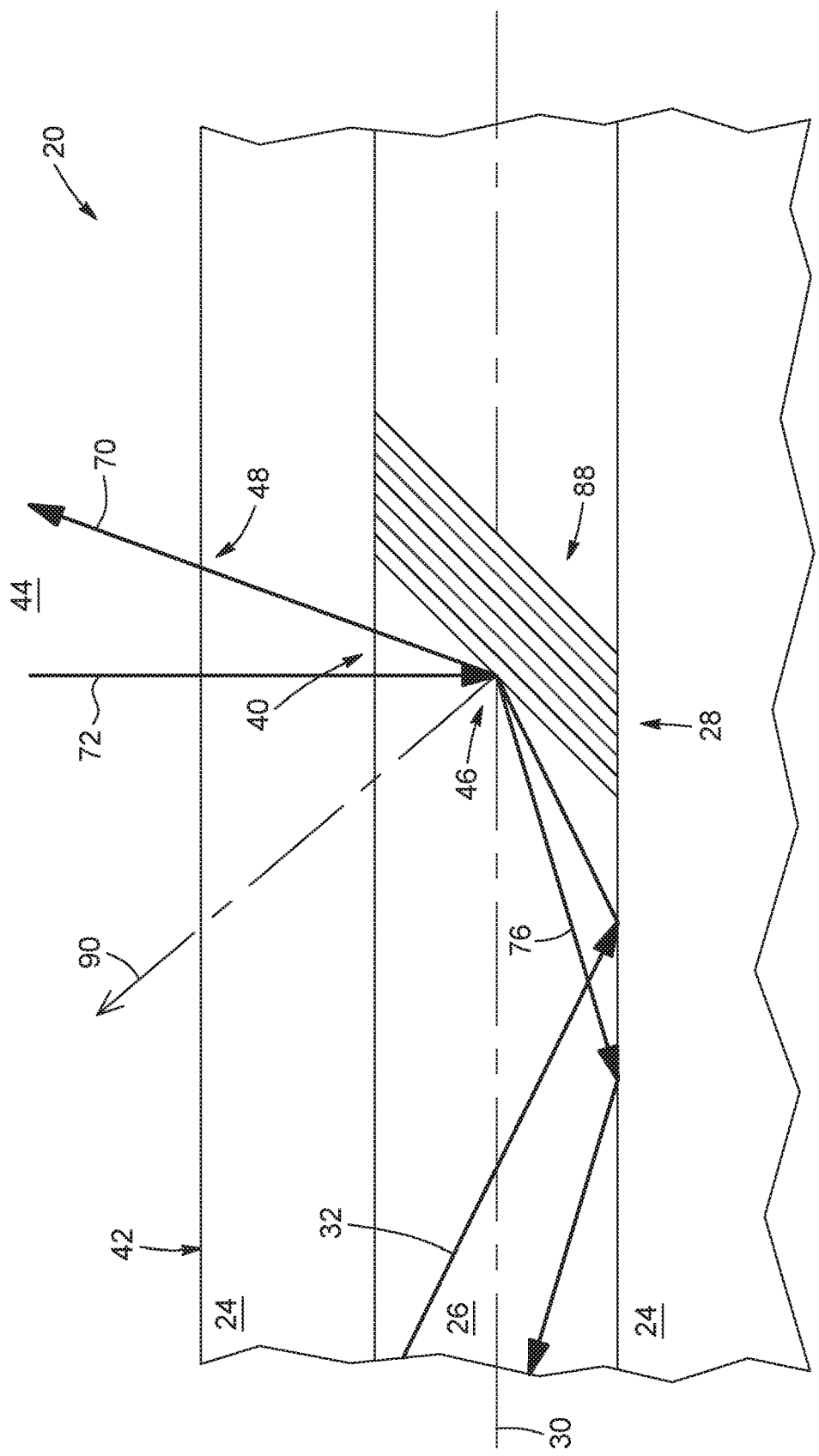
FIG. 12 is a schematic longitudinal cross-sectional view of a lateral coupling zone of a multicore optical fiber, in accordance with a fifth variant, in which the lateral coupling zone includes a light deflector disposed in the core.

Referring to FIG. 12, in another embodiment, the lateral coupling zone 28 can include a light deflector 88 disposed in the core 26 and enabling lateral coupling of light between the core 26 and the exterior 44 of the fiber 20. In the present description, the term "light deflector" refers to an optical element or a combination of optical elements which can deflect, at least partly, the optical path of light incident thereonto.

In the out-coupling configuration, the light deflector 88 is oriented such that guided light 32 traveling in the core 26 and hitting the light deflector 88 will be deflected generally laterally outwardly along a path that defines the optical coupling path 40 of the lateral coupling zone 28. As illustrated in FIG. 12, the optical coupling path 40 extends between an inner end 46 located on the light deflector 88 and an outer end 48 located on the outer lateral surface 42 of the fiber 20. Meanwhile, in the in-coupling configuration, the light deflector 88 is oriented such that external light 72 entering generally laterally into the fiber 20 at the outer end 48 of the optical coupling path 40 will be deflected into the core 26 for propagation therealong as collected light 76.

The light deflector 88 can be embodied by a reflecting, a refracting or a diffracting optical element, or a combination thereof. Non-limiting examples of light deflectors include dielectric reflectors (e.g., Bragg reflectors), metallic reflectors (e.g., plane and curved mirrors), diffraction gratings (e.g., fiber Bragg gratings and embedded photonic crystal structures), and filters (e.g., interference filters). By way of example, in the embodiment of FIG. 12, the light deflector 88 is embodied by a tilted fiber Bragg grating (FBG) whose grating axis 90 is tilted with respect to the light-guiding path 30, for example at a tilt angle of 45° or another appropriate tilt angle. The fiber Bragg grating can for example be inscribed in the core 26 by conventional laser processing techniques.

In some implementations, the light deflector 88 may be a wavelength-selective light reflector configured to enable lateral coupling only for light in a selected range of wavelengths. However, in other implementations, the light deflector 88 may not be spectrally selective and may provide lateral coupling of light over a broad spectral range. It will be understood that in some implementations using a fiber Bragg grating, lateral optical coupling may be facilitated if the core is single mode. This is because the operation of fiber Bragg gratings is based on additive coherent addition of local reflections from a locally periodic variation of the refractive index. This positive interference is wavelength- and mode-dependent (through their effective refractive index). In a multimode core, the coherent addition of all contributions cannot be mode-independent, which implies an overall reduced reflection.

Figure 13:
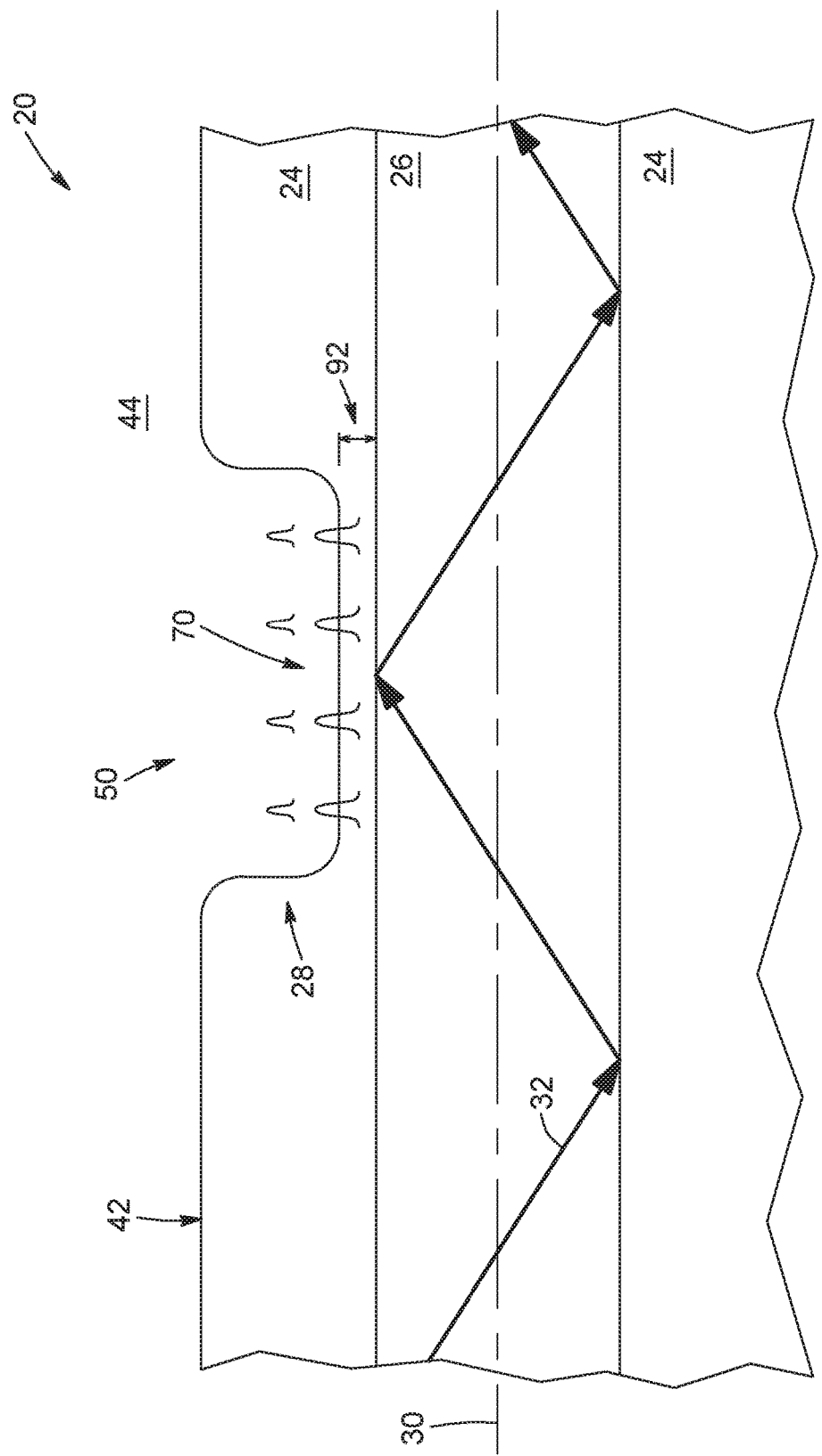
FIG. 13 is a schematic longitudinal cross-sectional view of a lateral coupling zone of a multicore optical fiber, in accordance with a sixth variant, in which lateral coupling of light is achieved by evanescent wave coupling.

Referring to FIG. 13, in yet another embodiment, the lateral coupling zone 28 can enable lateral coupling between the core 26 to the exterior 44 of the fiber 20 by evanescent-wave coupling. In this regard, it should be noted that while the embodiment of FIG. 13 illustrates a scenario where evanescent wave coupling is used to provide lateral out-coupling of light, lateral in-coupling of light by evanescent wave interaction may also be possible in some scenarios.

As known in the art, the evanescent field of light guided in the core of an optical fiber remains usually confined inside the cladding. This means that in order for the evanescent field to "leak out" of the fiber and interact with the surrounding medium (e.g. a sample or a region of interest), the evanescent field must be made to extend at least partly out of the fiber. Referring to FIG. 13, in some implementations, this can be achieved by locally etching, tapering, polishing or otherwise machining a region of the cladding 24 to reduce the thickness of the cladding 24 and bring the outer lateral surface 42 of the fiber 20 closer to the core 26. The machined region of the cladding 24 defines the lateral coupling zone 28 of the fiber 20.

Referring still to FIG. 13, in some implementations, the lateral coupling zone 28 includes a cavity 50 extending inwardly from the outer lateral surface 42 of the fiber 20 and terminating into the cladding 24 at a depth such that a lateral gap 92 remains between a bottom 94 of the cavity 50 and the core 26. This lateral gap 92 can be adjusted to fulfill the conditions for enabling lateral evanescent wave coupling between the core 26 and the exterior 44 of the fiber 20. That is, the evanescent field of the guided light 32 traveling in the core 26 is coupled out of the core 26 as delivered light 70. By way of example, in some non-limiting implementations, the lateral gap can have a thickness ranging from about 1 µm to about 5 µm. It will be understood that to provide multi-point quasi-distributed light delivery to a region or sample of interest, the cavity 50 defining the lateral coupling zone 28 generally has a limited extent both longitudinally (e.g., between about 100 µm and a few millimeters) and azimuthally (e.g., between about 50 µm and about 100 µm) on the outer lateral surface 42 of the fiber 20.

Optical Probing System

Figures 14, 14A:
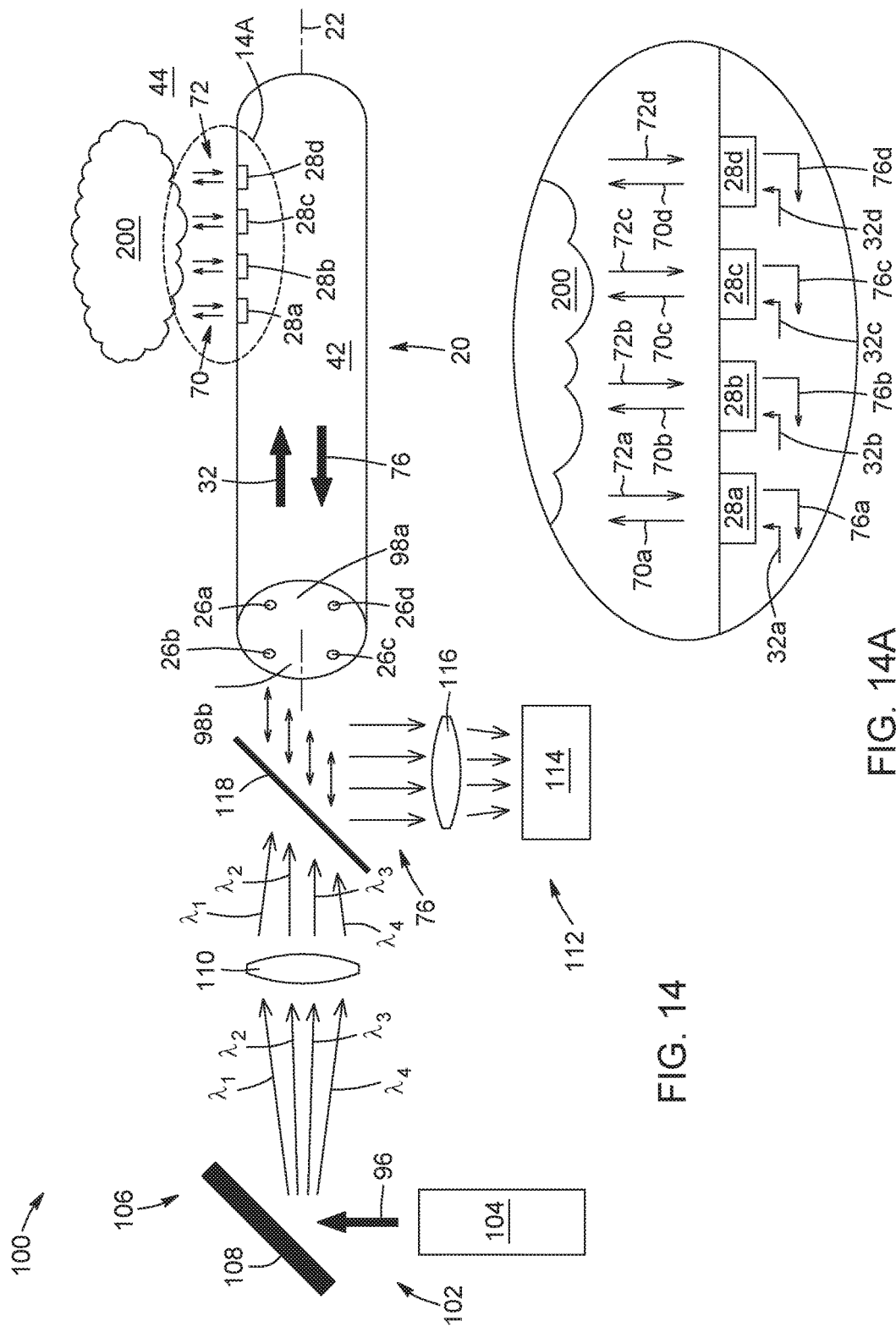
FIG. 14 is a schematic representation of an optical probing system for light delivery and light collection, in accordance with an embodiment.
FIG. 14A is an enlargement of portion 14A of FIG. 14.

Referring now to FIGS. 14 and 14A, in accordance with another aspect, there may be provided an optical probing system 100 for at least one of light delivery to and light collection from a probed region 200.

Depending on the application, the probed region 200 refers to any region of interest which the optical probing system disclosed herein can sense, detect, monitor, interrogate, excite, stimulate or otherwise probe by delivering light thereto and/or collecting light therefrom. The term "probed region" is to be interpreted broadly to encompass any object, structure, substance, material, person or other living organism, environment, medium or region of space to which light can transmitted and/or from which light can be received.

The optical probing system 100 first includes a multicore optical fiber 20 according to any one of the embodiments and variants described above or equivalents thereof. The multicore optical fiber 20 includes a cladding 24, multiple cores 26a to 26d disposed in the cladding 24 and extending helically about the fiber axis 22, and a set of lateral coupling zones 28a to 28d longitudinally distributed and azimuthally aligned with respect to the fiber axis 22. Each lateral coupling zone 28a to 28d forms an optical coupling path that enables either or both of: (i) coupling of guided light 32 out of a corresponding core 26a to 26d for delivery, as delivered light 70, to the probed region 200; and/or (ii) collection of incoming light 72 from the probed region for coupling, as collected light 76, into the corresponding core 26a to 26d.

Referring still to FIGS. 14 and 14A, in some implementations, the optical probing system 100 can also include a light injection assembly 102. The light injection assembly 102 is configured to inject light 96 into the multiple cores 26a to 26d for propagation therealong as the guided light 32. The guided light 32 is guided along the cores 26a to 26d until it reaches the set of lateral coupling zones 28a to 28d, at which point the guided light 32 is coupled out of the cores 26a to 26d via the lateral coupling zones 28a to 28d and delivered to the probed region 200 as probing light 70.

In the embodiment of FIGS. 14 and 14A, the light injection assembly 102 is configured to inject light into the multiple cores 26a to 26d via an input endface 98a of the multicore optical fiber 20. Since various optical coupling techniques are known in the art for injecting light through an endface of a multicore optical fiber, a detailed discussion of their structure and operation will not be provided herein. By way of example, some of these techniques can involve endface coupling through free-space optics, optical fibers, or multicore connectors. It is noted that because some implementations of the present techniques do not require the cores to be single mode, such implementations can facilitate the injection of light into the cores of the multicore fibers.

In the embodiment of FIGS. 14 and 14A, the light injection assembly 102 first includes a light source module 104 configured to generate input light 96 having multiple spectral components $\lambda_1$ to $\lambda_4$, each spectral component $\lambda_1$ to $\lambda_4$ having a wavelength selected from a plurality of different wavelengths. By way of example, four such spectral components $\lambda_1$ to $\lambda_4$ are used in the embodiment of FIGS. 14 and 14A. The light source module 104 can be embodied by any appropriate device or combination of devices able to generate input light for the intended probing application. In some implementations, the light source module 104 can include one or more laser sources configured to generate the input light 96 having the multiple spectral components $\lambda_1$ to $\lambda_4$. In other variants, different types of light sources can be used besides lasers sources, including, without limitation, light-emitting diodes (LEDs) and other broadband light sources. The choice of the light source module can be dictated by several factors depending on the application in which the optical probing system is intended to be used.

Referring still to FIGS. 14 and 14A, the light injection assembly 102 also includes injection optics 106 disposed in a path of the input light 96 generated by the light source module 104. The injection optics 106 can be embodied by any appropriate device or combination of devices able to split spectrally and spatially the input light 96 into its spectral components $\lambda_1$ to $\lambda_4$ along distinct paths, and to direct each one of the split spectral components $\lambda_1$ to $\lambda_4$ into a different corresponding one of the multiple cores 26a to 26d for coupling thereto via the input endface 98a of the multicore optical fiber 20. By way of example, in the embodiment of FIGS. 14 and 14A, the injection optics 106 includes a diffraction grating 108 to split the input light 96 into its spectral components $\lambda_1$ to $\lambda_4$, and focusing optics 110 (e.g., lenses) to focus each one of the split spectral components $\lambda_1$ to $\lambda_4$ into the corresponding cores 26a to 26d. Of course, various other arrangements for the injection optics can be used in other implementations.

It should be noted that while FIGS. 14 and 14A provide a multiple-wavelength implementation, in which each one of the cores 26a to 26d is injected with light having a specific wavelength, single-wavelength implementations, in which each one of the cores 26a to 26d is injected with light having the same wavelength, are also possible. In such scenarios, it will be understood that the injection optics splits the input light 96 only spatially, and not spectrally. For instance, the splitting of the input light 96 can be such that each one of the cores 26a to 26d receives the same amount of optical power.

Referring still to FIGS. 14 and 14A, the multiple spectral components $\lambda_1$ to $\lambda_4$ are injected into the multiple cores 26a to 26d as multiple guided signals that together form the guided light 32. The multiple guided signals propagate along the multiple cores 26a to 26d toward the set of lateral coupling zones 28a to 28d. Once they reach the set of lateral coupling zones 28a to 28d, the guided signals are successively coupled out of the cores 26a to 26d and delivered to the probed region 200 as a set of longitudinally distributed and azimuthally aligned probing signals 70a to 70d. The set of probing signals 70a to 70d forms the probing light 70 referred to above.

In the illustrated embodiment, the probing signals 70a to 70d interact with the probed region 200 and induce an optical response from the probed region 200. For example, each probing signal 70a to 70d may excite one of a plurality of probed sites (not shown) provided in the probed region 200. Without limitation, this optical response can include light emanating from the probed region 200 due to transmission, reflection, refraction, diffraction, scattering, interference, emission, absorption, and/or nonlinear optical phenomena. The incoming light 72 from the probed region 200 can be collected into the multicore fiber 20 as incoming light signals 72a to 72d via the set of lateral coupling zones 28a to 28d. That is, the lateral coupling zones 28a to 28d enable coupling of the incoming light signals 72a to 72d into the corresponding core 26a to 26d for propagation therealong as collected light signals 76a to 76d. The collected light signals together form the collected light 76.

Referring still to FIGS. 14 and 14A, in some implementations, the optical probing system 100 can further include a light detection assembly 112 configured to receive the collected light 76 from the multiple cores 26a to 26d after coupling therein via, and propagation therealong away from, the set of lateral coupling zones 28a to 28d. In the illustrated embodiment, the collected light 76 is emitted from the multiple cores 26a to 26d at the output endface 98b of the multicore optical fiber 20 which is the same as the input endface 98a. This is because the same lateral coupling zones 28a to 28d are used in this embodiment for both light delivery and light collection, with the result that the light to be delivered to and the light collected from the probed region 200 propagate in opposite directions between the lateral coupling zones and one of the fiber endface.

Figure 15:
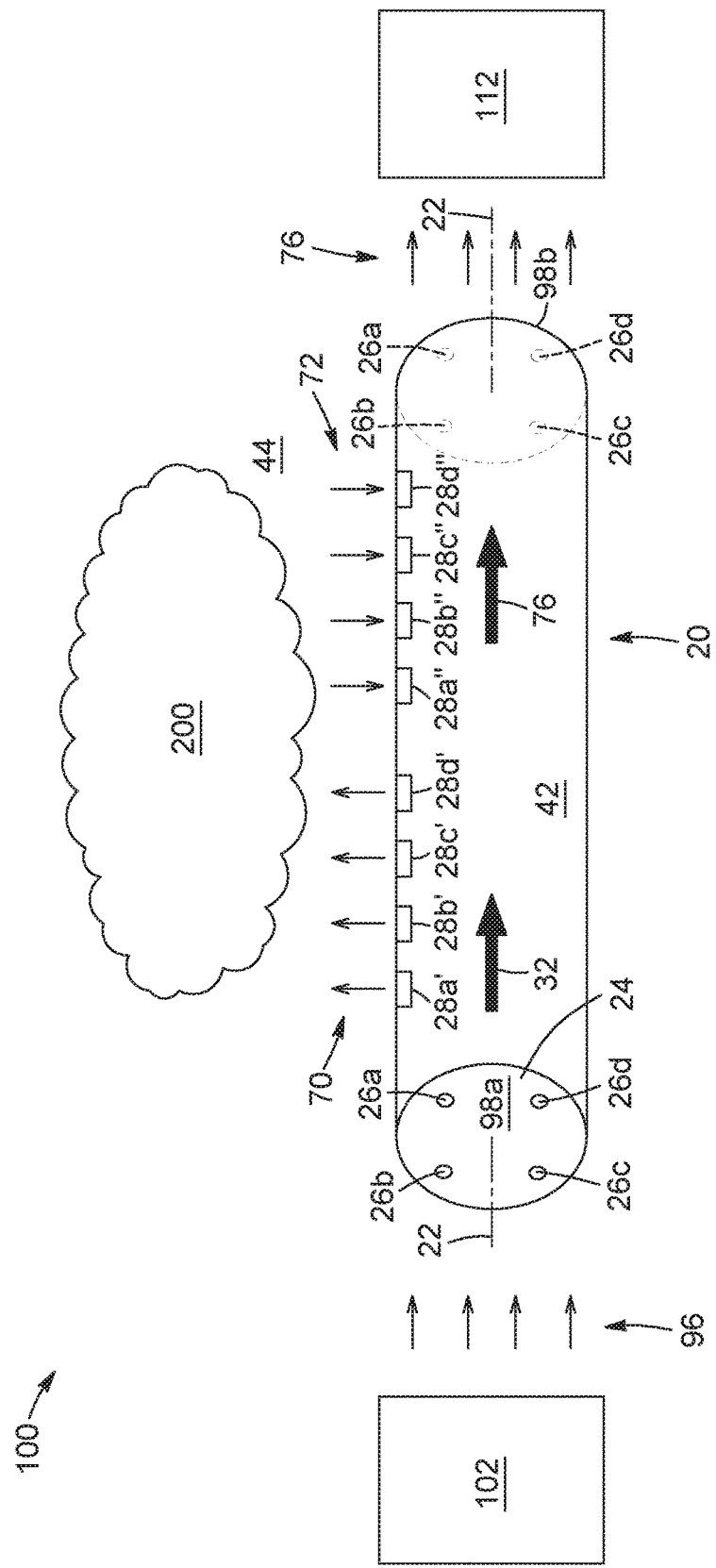
FIG. 15 is a schematic representation of an optical probing system for light delivery and light collection, in accordance with another embodiment, including two longitudinally spaced-apart sets of lateral coupling zones.

Turning briefly to FIG. 15, in another embodiment, the multicore fiber 20 can include a first set of lateral coupling zones 28a' to 28d' and a second set of lateral coupling zones 28a" to 28d" provided downstream of the first set with respect to the direction of light propagation in the fiber 20. In this embodiment, the light injection assembly 102 is configured to inject light 96 into the cores 26a to 26d via the endface 98a of the fiber 20. The injected light propagates as guided light 32 along the cores 26a to 26d until it reaches the first set of lateral coupling zones 28a' to 28d'. There, the guided light 32 is coupled out of the cores 26a to 26d and delivered as probing light 70 to the probed region 200. Meanwhile, incoming light 72 from the probed region 200 is coupled into the cores 26a to 26d via the second set of lateral coupling zones 28a" to 28d" and guided along the cores 26a to 26d toward the opposite endface 98b of the fiber 20. There, the collected light 76 is outputted from the fiber 20 and directed to the light detection assembly 112.

Returning to FIGS. 14 and 14A, the light detection assembly 112 can include an optical detector 114 and suitable detection optics 116. The optical detector 114 can be embodied by any appropriate device or combination of devices able to detect the light 76 collected from the probed region 200 and outputted from the multiple cores 26a to 26d as different collected light signals. The detection optics 116 can be embodied by any optical components arranged to provide an optical path for the collected light as it travels from the output endface 98b of the fiber 20 to the optical detector 114. The detection optics 116 can include lenses, mirrors, filters, and any other suitable reflective, refractive and/or diffractive optical components.

The choice of the optical detector can be dictated by several factors depending on the nature of the application in which the optical probing system is used, notably the types of optical phenomenon that are to be detected and analyzed. In some implementations, the optical detector 114 can be embodied by various types of square law detectors and spectral detectors including, without limitation, a photodiode array, a photomultiplier array, a complementary metal-oxide-semiconductor (CMOS) array, a charge-coupled device (CCD) array, a charge injection device (CID) array, another type of pixelated or non-pixelated detector, a spectrometer, an optical spectrum analyzer, an optical vector analyzer, or another type of spectral measuring device. The signal(s) from the optical detector 114 output can be subsequently processed and analyzed to yield information about the probed region 200.

As mentioned above, in the illustrated embodiment, the same fiber endface is used for both injecting the guided light 32 into and outputting the collected light 76 from the multiple cores 26a to 26d. In such scenarios, a light separator 118, may be provided to separate the collected light 76 outputted from the fiber 20 from the input light 96 to be injected in the fiber 20. Depending on the application, the light separator 118 can be embodied by various optical components including, without limitation, an optical circulator, a directional coupler, a multi-channel optical add-drop multiplexer, or a dichroic filter in cases where the injection light and the collected light have different wavelengths.

Figure 16:
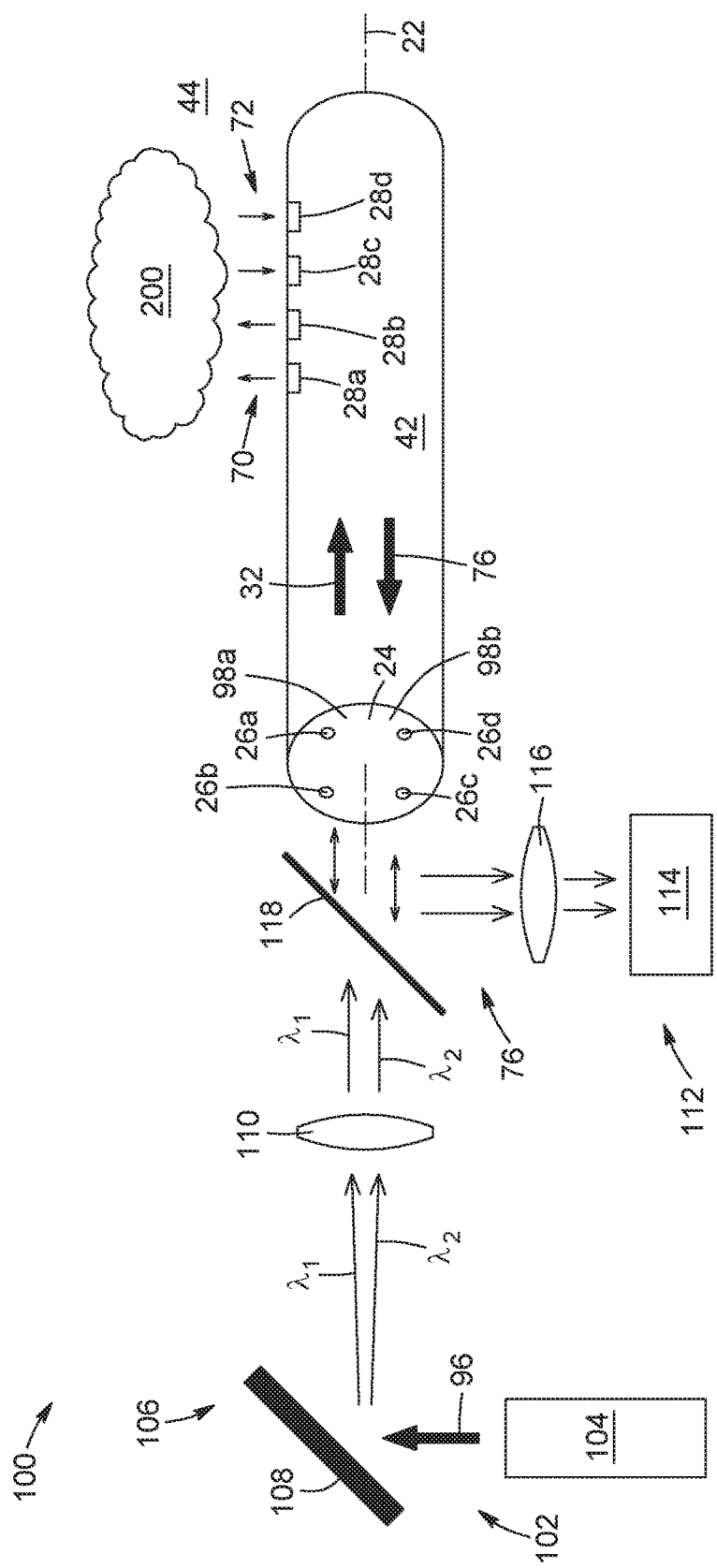
FIG. 16 is a schematic representation of an optical probing system for light delivery and light collection, in accordance with another embodiment, in which each lateral coupling zone is used either for light delivery or light collection.

It is noted that in the embodiment of FIGS. 14 and 14A, each one of the lateral coupling zones 28a to 28d is used for both light delivery and light collection. Turning to FIG. 16, in other embodiments, each one of the lateral coupling zones 28a to 28d may be used only for either light delivery (i.e., coupling zones 28a and 28b in FIG. 16) or light collection (i.e., coupling zones 28c and 28d in FIG. 16). In such scenarios, the configuration of the lateral coupling zones 28a and 28b used for light delivery can differ from the configuration of the lateral coupling zones 28c and 28d used for light collection, for example if the delivered light and the collected light have different wavelengths.

In yet other variants, one or more coupling zones in the set may be used for unidirectional coupling (either in-coupling or out-coupling), while the remainder of the set may be used for bidirectional coupling.

Figure 17:
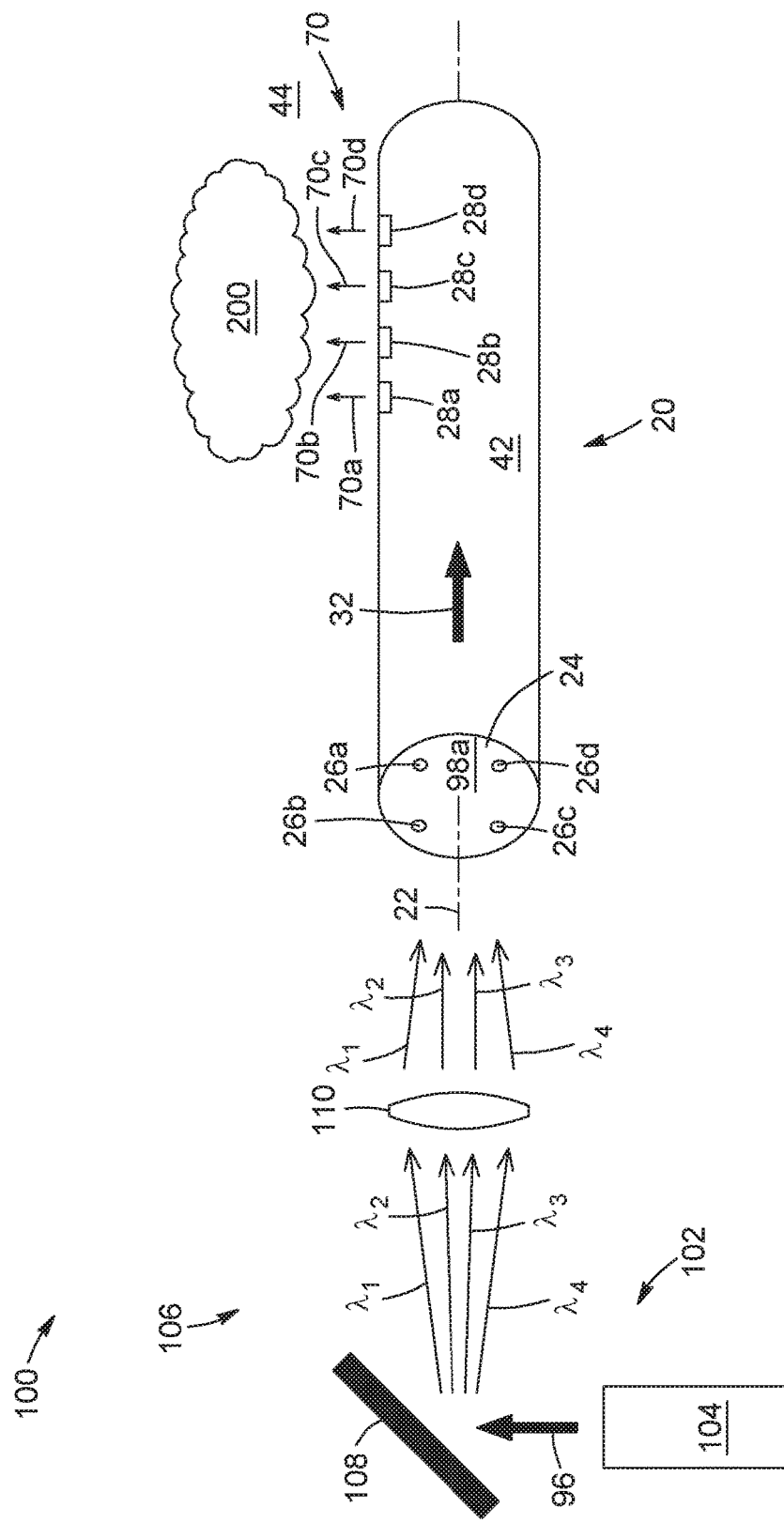
FIG. 17 is a schematic representation of an optical probing system for light delivery, in accordance with another embodiment, in which all the lateral coupling zones are used only for light delivery.

Referring to FIG. 17, in another embodiment, the optical probing system 100 can be used only for light delivery to a probed region 200. In this embodiment, the optical probing system 100 can include a multicore optical fiber 20 and a light injection assembly 102, but no light detection assembly. The light injection assembly 102 can be configured to inject light 96 into the multiple cores 26a to 26d of the fiber 20 for propagation therealong as guided light 32. The guided light 32 is guided along the cores 26a to 26d until it reaches the set of lateral coupling zones 28a to 28d, at which point the guided light 32 is coupled out of the cores 26a to 26d via the lateral coupling zones 28a to 28d and delivered to the probed region 200 as probing signals 70a to 70d forming probing light 70. In such scenarios, the delivery of the probing light 70 to the probed region 200 may or may not elicit an optical response from the probed region 200, but if it does, then any resulting light emanating from the probed region 200 will not be collected by the lateral coupling zones 28a to 28d of the fiber 20.

Referring to FIG. 18, in a further embodiment, the optical probing system 100 can be used only for light collection from a probed region 200. In this embodiment, the optical probing system 100 can include a multicore optical fiber 20 and a light detection assembly 112, but no light injection assembly. Light 72 originating from the probed region 200 can be coupled into the fiber 20 as collected light 76 through the set of lateral coupling zones 28a to 28d. This collected light 76 can be guided along the multiple cores 26a to 26d toward the output endface 98b of the fiber 20. There, the collected light 76 escapes from the fiber 20 and is directed to the light detection assembly 112. In such scenarios, the light 72 originating from the probed region 200 may or may not have been induced by an applied optical excitation, but if it is, then this optical excitation is not applied to the probed region 200 via the lateral coupling zones 28a to 28d of the fiber 20.

Figure 19:
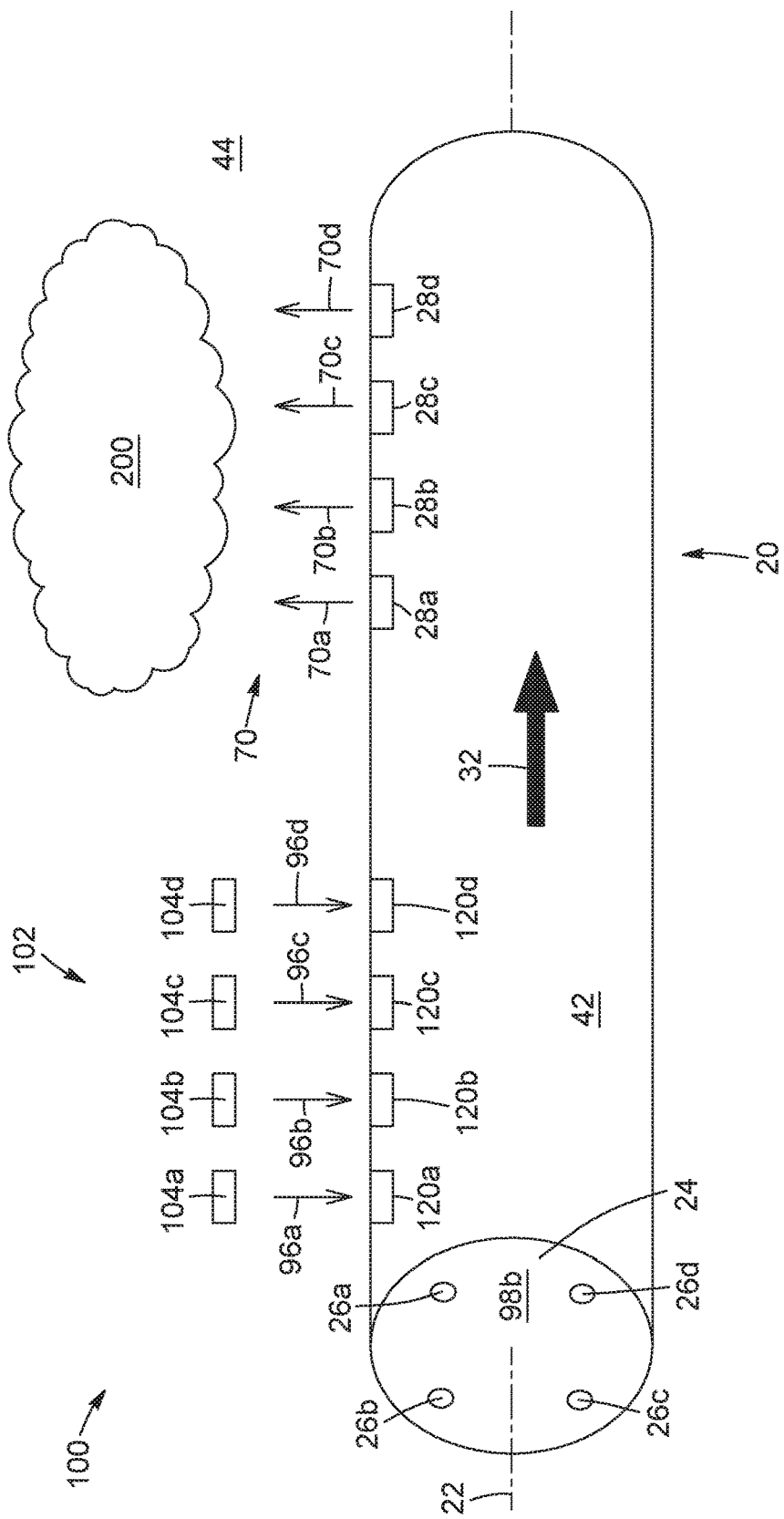
FIG. 19 is a schematic representation of an optical probing system for light delivery, in accordance with another embodiment, including a set of lateral coupling zones for light delivery to a probed region and an additional set of lateral coupling zones coupled to a light injection assembly.

Referring to FIG. 19, in another embodiment, the optical probing system 100 can include yet another set of lateral coupling zones 120a to 120d in addition to a set of lateral coupling zones 28a to 28d used for light delivery to the probed region 200. The additional set of lateral coupling zones 120a to 120d is coupled to the light injection assembly 102 to enable individual injection of input light signals 96a to 96d into each one of the multiple cores 26a to 26d. To this end, the light injection assembly 102 can include a linear array of laser diodes 104a to 104d, each one of the laser diodes 104a to 104d emitting a respective one of the input light signals. The array of laser diodes 104a to 104d is arranged with respect to the additional set of lateral coupling zones 120a to 120d such that each one of the laser diodes 104a to 104d directs its respective input light signal 96a to 96d into the corresponding coupling zone 120a to 120d of the additional set for coupling into and propagation as guided light 32 along the corresponding one of the multiple cores 26a to 26d of the fiber 20. In some variants, a coplanar array of parallel optical fibers can be used instead of a linear array of laser diodes to inject the input light signals 96a to 96d into the additional set of lateral coupling zones 120a to 120d. The guided light 32 is guided along the cores 26a to 26d until it reaches the set of lateral coupling zones 28a to 28d, at which point the guided light 32 is coupled out of the cores 26a to 26d via the lateral coupling zones 28a to 28d and delivered to the probed region 200 as probing signals 70a to 70d.

Figure 20:
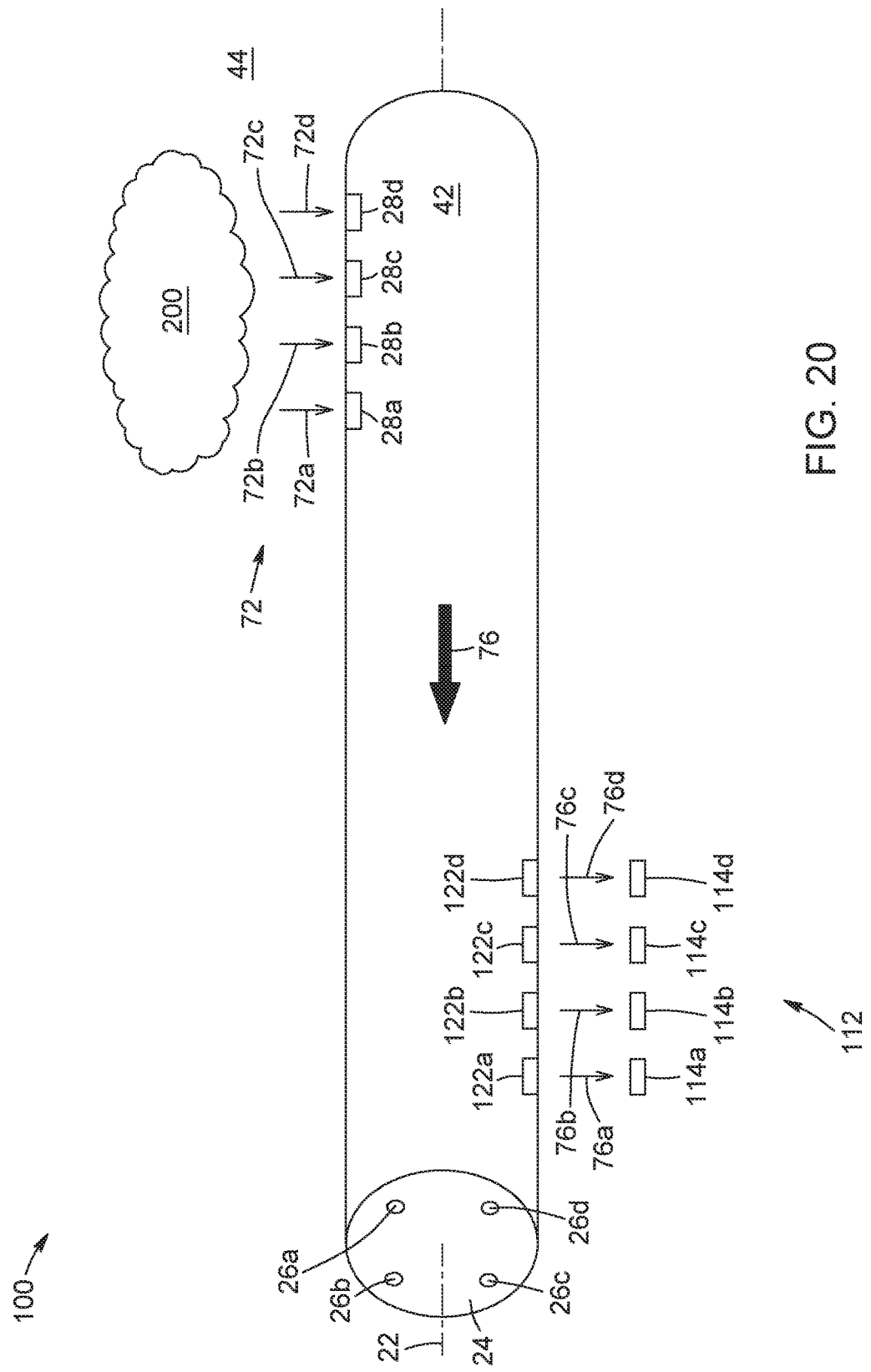
FIG. 20 is a schematic representation of an optical probing system for light collection, in accordance with another embodiment, including a set of lateral coupling zones for light collection from a probed region and an additional set of lateral coupling zones coupled to a light detection assembly.

Referring to FIG. 20, in another embodiment, the optical probing system 100 can include a set of lateral coupling zones 122a to 122d in addition to a set of lateral coupling zones 28a to 28d used for light collection from the probed region 200. Light signals 72a to 72d originating from the probed region 200 can be coupled into the fiber 20 as collected light signals 76a to 76d through the set of lateral coupling zones 28a to 28d. The collected light signals 76a to 76d are guided as collected light 76 along the multiple cores 26a to 26d. The additional set of lateral coupling zones 122a to 122d is used to couple the collected light signals 76a to 76d individually out of each of the multiple cores 26a to 26d. The light detection assembly 112 can include a linear array of photodetectors 114a to 114d arranged with respect to the fiber 20 in such a way that each of the photodetectors 114a to 114d receives and detects a respective one of the collected light signals 76a to 76d outputted from the additional lateral coupling zones 122a to 122d.

Returning to the embodiment of the multicore optical fiber 20 illustrated in FIGS. 1 to 3 and 4A to 4D, it is noted that, for some applications, the lateral coupling zones 28a to 28d of the fiber 20 may be used for light injection into the cores 26a to 26d from a light injection assembly and/or light extraction from the cores 26a to 26d for detection by a light detection assembly, but not for light delivery to and/or light collection from a probed region.

It is also noted that in other applications, the multicore optical fiber disclosed herein can be used for one, some, or all of light delivery to a probed region, light collection from a probed region, light injection from a light injection assembly and light extraction for detection by a light detection assembly.

Of course, numerous modifications could be made to the embodiments described above without departing from the scope of the appended claims.

The invention claimed is:

1. A multicore optical fiber having a fiber axis, the multicore optical fiber comprising:
a cladding;
multiple cores disposed in the cladding, each one of the multiple cores following a helical trajectory about the fiber axis; and
a set of lateral coupling zones longitudinally distributed and azimuthally aligned with respect to the fiber axis, each one of the lateral coupling zones forming an optical coupling path extending and enabling lateral coupling of light between a corresponding one of the multiple cores and an exterior of the multicore optical fiber.

2. The multicore optical fiber of claim 1, wherein at least one of the lateral coupling zones comprises a cavity extending inwardly from an outer lateral surface of the multicore optical fiber toward a corresponding one of the multiple cores.

3. The multicore optical fiber of claim 2, wherein the cavity extends at least partly into the corresponding core and defines an optical interface therebetween.

4. The multicore optical fiber of claim 3, wherein the optical interface is oriented with respect to the corresponding core to enable the lateral coupling of light to be effected via total internal reflection inside the corresponding core at the optical interface.

5. The multicore optical fiber of claim 3, wherein the at least one of the lateral coupling zones further comprises a light reflector disposed inside the cavity and along the optical coupling path.

6. The multicore optical fiber of claim 5, wherein the light reflector comprises a reflective layer deposited on a wall of the cavity.

7. The multicore optical fiber of claim 5, wherein the light reflector comprises a reflective microsphere.

8. The multicore optical fiber of claim 2, wherein the cavity is filled at least partly with a material having a refractive index different than a refractive index of the corresponding core.

9. The multicore optical fiber of claim 2, wherein the at least one of the lateral coupling zones further comprises focusing optics arranged on the outer lateral surface of the multicore optical fiber and extending over and across an opening of the cavity.

10. The multicore optical fiber of claim 2, wherein the cavity is spaced outwardly from the corresponding core in a manner such that a lateral gap is formed therebetween, the lateral gap enabling evanescent wave coupling of light thereacross between the corresponding core and the exterior of the multicore fiber.

11. The multicore optical fiber of claim 2, wherein the cavity is formed by laser processing.

12. The multicore optical fiber of claim 1, wherein at least one of the lateral coupling zones comprises a light deflector arranged in the corresponding core.

13. The multicore optical fiber of claim 12, wherein the light deflector comprises a fiber Bragg grating, the fiber Bragg grating having a grating axis tilted with respect to a light-guiding path of the corresponding core.

14. The multicore optical fiber of claim 1, wherein, in a cross-section of the fiber, the multiple cores are arranged along a perimeter of a closed-shape figure centered with respect to the fiber axis.

15. The multicore optical fiber of claim 1, wherein at least one of the lateral coupling zones is configured to couple light from the corresponding one of the multiple cores to the exterior of the multicore optical fiber.

16. The multicore optical fiber of claim 1, wherein at least one of the lateral coupling zones is configured to couple light from the exterior of the multicore optical fiber to the corresponding one of the multiple cores.

17. The multicore optical fiber of claim 1, wherein at least one of the lateral coupling zones is configured to couple light both out of and into the corresponding one of the multiple cores.

18. The multicore optical fiber of claim 1, wherein the helical trajectory of each core has a spatial repetition period ranging from 5 millimeters to 50 centimeters.

19. The multicore optical fiber of claim 1, wherein adjacent ones of the lateral coupling zones are spaced-apart by a distance ranging from 100 micrometers to 10 centimeters.

20. The multicore optical fiber of claim 1, wherein the multiple cores comprise between 2 and 50 cores.

21. The multicore optical fiber of claim 1, wherein the helical trajectories followed by the multiple cores result from a permanent spin imparted to the multicore optical fiber.

22. The multicore optical fiber of claim 1, wherein each one of the multiple cores follows the helical trajectory along an entire length thereof.

23. The multicore optical fiber of claim 1, further comprising a centered core coaxially aligned with and following a straight trajectory along the fiber axis.

24. An optical probing system for at least one of light delivery to and light collection from a probed region, the optical probing system comprising a multicore optical fiber having a fiber axis and comprising a cladding, multiple cores disposed in the cladding and extending helically about the fiber axis, and a set of lateral coupling zones longitudinally distributed and azimuthally aligned with respect to the fiber axis, each one of the lateral coupling zones forming an optical coupling path enabling at least one of:
lateral coupling of guided light out of a corresponding one of the multiple cores for delivery to the probed region; and
collection of incoming light from the probed region for lateral coupling into the corresponding one of the multiple cores.

25. The optical probing system of claim 24, further comprising a light injection assembly configured to inject the guided light into the multiple cores.

26. The optical probing system of claim 24, further comprising a light detection assembly configured to receive the collected light from the multiple cores.

27. The optical probing system of claim 24, further comprising an additional set of lateral coupling zones and at least one of:
- a light injection assembly coupled to the additional set of lateral coupling zones and configured to inject the guided light into the multiple cores; and
- a light detection assembly coupled to the additional set of lateral coupling zones and configured to receive the collected incoming light from the multiple cores.

* * * * *